(12) United States Patent
Robbins et al.

(10) Patent No.: US 7,786,315 B2
(45) Date of Patent: Aug. 31, 2010

(54) PROCESS FOR SELECTIVELY EXTRACTING PROCYANIDINS

(75) Inventors: Rebecca J. Robbins, Budd Lake, NJ (US); Mark A. Kelm, Fresno, CA (US); John P. Munafo, Hackettstown, NJ (US)

(73) Assignee: Mars, Inc., McLean, VA (US)

( * ) Notice: Subject to any disclaimer, the term of this patent is extended or adjusted under 35 U.S.C. 154(b) by 69 days.

(21) Appl. No.: 12/342,321

(22) Filed: Dec. 23, 2008

(65) Prior Publication Data

US 2009/0203926 A1 Aug. 13, 2009

Related U.S. Application Data

(62) Division of application No. 11/242,473, filed on Oct. 3, 2005, now Pat. No. 7,485,735.

(51) Int. Cl.
*C07D 311/62* (2006.01)
(52) U.S. Cl. ...................... 549/399; 424/776
(58) Field of Classification Search ................ 549/399; 424/776
See application file for complete search history.

(56) References Cited

U.S. PATENT DOCUMENTS 6,627,232 B1   9/2003   Hammerstone et al.

FOREIGN PATENT DOCUMENTS

WO    WO 2008/051799 A2    2/2008

OTHER PUBLICATIONS

A. Yanagida et al., J. Chromatog A (2000) 890:251-259.

*Primary Examiner*—Bernard Dentz

(57) ABSTRACT

A process is described for selectively extracting cocoa procyanidins from an aqueous mixture of cocoa polyphenols by using a particular sequence of solvents to extract selected procyanidin monomers and/or oligomers. The solvents are n-butyl acetate, ethyl acetate, methyl acetate, diethyl ether, or mixtures of methyl acetate and diethyl ether. Preferably, the aqueous mixture of cocoa polyphenols is first extracted with n-butyl acetate. The mixtures of methyl acetate and diethyl ether are between 25:75 and 75:25 (v/v).

10 Claims, 20 Drawing Sheets

(1/4)

(2/4)

(3/4)

(4/4)

(1/4)

(2/4)

(3/4)

(4/4)

PROCESS FOR SELECTIVELY EXTRACTING PROCYANIDINS

CROSS-REFERENCE TO RELATED APPLICATIONS

This application is a division of Ser. No. 11/242,473 filed Oct. 3, 2005 for Process for Selectively Extracting Procyanidins, now U.S. Pat. No. 7,485,737.

BACKGROUND OF THE INVENTION

1. Field of the Invention

The present invention is directed to a process for selectively extracting cocoa procyanidins according to their degree of polymerization, using particular sequences of solvents. In particular, the present invention is directed to a process for selectively extracting individual oligomers or small groups of oligomers from a mixture of cocoa procyanidins, using n-butyl acetate as the first extraction solvent.

It is known that individual flavan-3-ols, such as catechin, epicatechin and cocoa procyanidin oligomers, exhibit distinct properties and have distinct applications for human and animal use. Selectively extracting specific monomers or oligomers on the basis of degree of polymerization will allow for more targeted and efficacious use thereof, in pharmacological applications, as well as in food-grade products.

2. Discussion of the Related Art

Proanthocyanidins, the oligomers and polymers of flavan-3-ols, are the second most abundant natural plant phenol after lignin. The flavan-3-ol subunits are linked primarily through a carbon-carbon bond from the 4 position of one subunit to the 8 position of another subunit (C4→C8), and to a lesser extent through C4→C6 linkage.

Procyanidins represent the largest class of proanthocyanidins. Gu et al. showed that out of 41 foods found to contain proanthocyanidins, 27 contained procyanidins. (J. Agric. and Food Chem. 51 (2003) 7513). Procyanidins typically consist of (−)-epicatechin, (+)-epicatechin, (−)-catechin and/or (+)-catechin subunits.

Procyanidins include B-type and A-type proanthocyanidins. In B-type proanthocyanidins, the monomeric subunits (catechin, epicatechin) are connected via interflavan linkages of C4→C6 and/or C4→C8. Oligomers with exclusively C4→C8 linkages are linear, while the presence of at least one C4→C6 bond results in a branched oligomer. By contrast, A-type proanthocyanidins are doubly-linked oligomers, containing linkages C2-O-C7 and C4→C6 or C4→C8.

The molecular weight of proanthocyanidins typically is expressed as degree of polymerization (DP), and individual oligomers are commonly referred to as dimers, trimers, etc.

It is known that individual procyanidin oligomers present specific characteristics and potential benefits for use in humans and animals. For example, Tempesta discloses that procyanidin oligomers having a degree of polymerization (DP) of 2-11 possess significant antiviral activity, and are useful in treating warm-blooded animals, including humans, infected with paramyxovaridae such as respiratory syncytial virus, orthomyxovaridae such as influenza A, B and C, and herpes viruses such as Herpes Simplex virus. (U.S. Pat. No. 5,211,944). Romanczyk Jr., et al. disclose antineoplastic compositions comprising procyanidin oligomers having a DP of 3-11 together with a suitable carrier. (U.S. Pat. No. 5,554,645). Romanezyk, Jr. et al. also disclose that procyanidin oligomers having a DP of 5-12 are useful as antioxidants. (U.S. Pat. No. 5,891,905). Schmitz et al. disclose the use of cocoa procyanidin oligomers (DP of 2-18) together with acetylsalicylic acid as anti-platelet therapy. (U.S. Pat. No. 6,524,630).

Significant improvements in the separation and resolution of procyanidin oligomers have been achieved. (See, Rigaud et al., Chromatogr. 654 (1993) 179; Cheynier et al., Methods in Enzymology 299 (1999); Natsume et al., Biosci. Biotechnol. Biochem. 64 (2000) 2581). Resolution of procyanidin oligomers up to the pentamer (DP=5) has been obtained. Hammerstone et al. disclosed modifications of this method, leading to improvements in resolution of monomers through the nonamers in the analysis of unfermented cacao seeds. (J. Agric. and Food Chem. 47 (1999) 490). Gu et al. disclosed still further improvements, leading to the elution of a polymer peak (DP>10), as well as enhancement in overall peak shape and resolution. (J. Agric. and Food Chem. 50 (2002) 4852).

It would be desirable to be able to maximize the loading capacity of cocoa procyanidins onto a preparative scale HPLC system, so that greater quantities of desired specific monomers and/or oligomers could be eluted for further study or use. Theoretically, the loading capacity of a preparative scale HPLC column (300×55 mm, 100 μm) is approximately 4 g of material. However, cocoa procyanidin extracts present solubility problems that limit the maximum loading capacity to approximately 400 mg, of which only approximately 41% are flavonoids.

It is expected that a significant increase in sample loading (flavanol) content can be achieved via selective extraction of individual or small groups of oligomers from a polyphenol mixture, prior to insertion onto an HPLC column. Accordingly, what is needed is a method for selectively extracting other desired cocoa procyanidin oligomers from an aqueous extract of cocoa polyphenols on the basis of degree of polymerization.

BRIEF SUMMARY OF THE INVENTION

The present invention provides a process for selectively extracting cocoa procyanidins from an aqueous mixture of cocoa polyphenols, by extracting the aqueous mixture with n-butyl acetate and separating an aqueous phase and an n-butyl acetate phase. The aqueous phase is enriched in procyanidin dimers and higher oligomers and the n-butyl acetate phase is enriched in catechin and epicatechin.

In a preferred embodiment, the aqueous phase enriched in procyanidin dimers and higher oligomers is extracted with an organic solvent which is either diethyl ether or a mixture of methyl acetate and diethyl ether effective to selectively extract catechin, epicatechin and procyanidin dimers, and the phases are separated. The aqueous phase is enriched in procyanidin trimers and higher oligomers and the organic phase is enriched in procyanidin dimers. Preferably, the mixture of methyl acetate and diethyl ether is approximately 25:75 (v/v). Further in this embodiment, the aqueous phase enriched in procyanidin trimers and higher oligomers is extracted with ethyl acetate and the phases are separated. The aqueous phase is enriched in procyanidin pentamers and higher oligomers and the ethyl acetate phase is enriched in procyanidin trimers and tetramers. Still further in this embodiment, the aqueous phase enriched in procyanidin pentamers and higher oligomers is extracted with an organic solvent which is a mixture of methyl acetate and diethyl ether effective to selectively extract catechin, epicatechin and procyanidin dimers, trimers, tetramers and pentamers, and the phases are separated. The aqueous phase is enriched in procyanidin hexamers and higher oligomers and the organic phase is enriched in procyanidin pentamers. Preferably, the mixture of methyl acetate and diethyl ether is approximately 75:25 (v/v). Still further in this embodiment, the aqueous phase enriched in procyanidin hexamers and higher oligomers is extracted with methyl acetate and the phases are separated. The aqueous phase is enriched in procyanidin nonamers and higher oligomers and the methyl acetate phase is enriched in procyanidin hexamers, heptamers and octamers. Still further in this embodiment, the aqueous phase enriched in procyanidin nonamers and higher oligomers is extracted with methyl acetate and the phases are separated. The methyl acetate phase is enriched in procyanidin nonamers and higher oligomers.

In another embodiment, the aqueous phase enriched in procyanidin trimers and higher oligomers is extracted with methyl acetate and the phases are separated. The aqueous phase is enriched in procyanidin nonamers and higher oligomers and the methyl acetate phase is enriched in procyanidin trimers, tetramers, pentamers, hexamers, heptamers and octamers. Further in this embodiment, the solvent is removed from the methyl acetate phase, the resulting product is dissolved in water, and the dissolved product is extracted with ethyl acetate. The phases are separated, with the aqueous phase being enriched in procyanidin pentamers, hexamers, heptamers and octamers and the ethyl acetate phase being enriched in procyanidin trimers and tetramers. Further in this embodiment, the aqueous phase enriched in procyanidin pentamers, hexamers, heptamers and octamers is extracted with an organic solvent which is a mixture of methyl acetate and diethyl ether effective to selectively extract catechin, epicatechin and procyanidin dimers, trimers, tetramers and pentamers and the phases are separated. The aqueous phase is enriched in procyanidin hexamers, heptamers and octamers and the organic phase is enriched in procyanidin pentamers. Preferably, the mixture of methyl acetate and diethyl ether is approximately 75:25 (v/v). Also in this embodiment, the aqueous phase enriched in procyanidin nonamers and higher oligomers is extracted with methyl acetate and the phases are separated. The methyl acetate phase is enriched in procyanidin nonamers and higher oligomers.

In another embodiment, the aqueous phase enriched in procyanidin dimers and higher oligomers is extracted with ethyl acetate and the phases are separated. The aqueous phase is enriched in procyanidin pentamers and higher oligomers and the ethyl acetate phase is enriched in procyanidin dimers, trimers and tetramers. In this embodiment, the aqueous phase enriched in procyanidin pentamers and higher oligomers is extracted with an organic solvent which is a mixture of methyl acetate and diethyl ether effective to selectively extract catechin, epicatechin and procyanidin dimers, trimers, tetramers and pentamers and the phases are separated. The aqueous phase is enriched in procyanidin hexamers and higher oligomers and the organic phase is enriched in procyanidin pentamers. Preferably, the mixture of methyl acetate and diethyl ether is approximately 75:25 (v/v). Further in this embodiment, the aqueous phase enriched in procyanidin hexamers and higher oligomers is extracted with methyl acetate and the phases are separated. The aqueous phase is enriched in procyanidin nonamers and higher oligomers and the methyl acetate phase is enriched in procyanidin hexamers, heptamers, and octamers. Still further in this embodiment, the aqueous phase enriched in procyanidin nonamers and higher oligomers is extracted with methyl acetate and the phases are separated. The methyl acetate phase is enriched in procyanidin nonamers and higher oligomers. Also in this embodiment, the solvent is removed from the ethyl acetate phase, the resulting product is dissolved in water, and the dissolved product is extracted in an organic solvent which is either diethyl ether or a mixture of methyl acetate and diethyl ether effective to selectively extract catechin, epicatechin and procyanidin dimers. The phases are separated. The aqueous phase is enriched in procyanidin trimers and tetramers and the organic phase is enriched in procyanidin dimers. Preferably, the mixture of methyl acetate and diethyl ether is approximately 25:75 (v/v). Alternatively in this embodiment, the aqueous phase enriched in procyanidin pentamers and higher oligomers is extracted with methyl acetate and the phases are separated. The aqueous phase is enriched in procyanidin nonamers and higher oligomers and the methyl acetate phase is enriched in procyanidin pentamers, hexamers, heptamers and octamers. Also in this alternative, the solvent is removed from the methyl acetate phase, the resulting product is dissolved in water, and the dissolved product is extracted with an organic solvent which is a mixture of methyl acetate and diethyl ether effective to selectively extract catechin, epicatechin and procyanidin dimers, trimers, tetramers and pentamers. The phases are separated. The aqueous phase is enriched in procyanidin hexamers, heptamers and octamers and the organic phase is enriched in procyanidin pentamers. Preferably, the mixture of methyl acetate and diethyl ether is approximately 75:25 (v/v).

In another embodiment, the aqueous phase enriched in procyanidin dimers and higher oligomers is extracted with an organic solvent which is a mixture of methyl acetate and diethyl ether effective to selectively extract catechin, epicatechin and procyanidin dimers, trimers, tetramers and pentamers, and the phases are separated. The aqueous phase is enriched in procyanidin hexamers and higher oligomers and the organic phase is enriched in procyanidin dimers, trimers, tetramers and pentamers. Preferably, the mixture of methyl acetate and diethyl ether is approximately 75:25 (v/v). In this embodiment, the aqueous phase enriched in procyanidin hexamers and higher oligomers is extracted with methyl acetate and the phases are separated. The aqueous phase is enriched in procyanidin nonamers and higher oligomers and the methyl acetate phase is enriched in procyanidin hexamers, heptamers and octamers. Further in this embodiment, the aqueous phase enriched in procyanidin nonamers and higher oligomers is extracted with methyl acetate and the phases are separated. The methyl acetate phase is enriched in procyanidin nonamers and higher oligomers. Alternatively in this embodiment, the solvent is removed from the organic phase enriched in procyanidin dimers, trimers, tetramers and pentamers, the resulting product is dissolved in water, and the dissolved product is extracted with an organic solvent which is either diethyl ether or a mixture of methyl acetate and diethyl ether effective to selectively extract catechin, epicatechin and procyanidin dimers. The phases are separated. The aqueous phase is enriched in procyanidin trimers, tetramers and pentamers and the organic phase is enriched in procyanidin dimers. Preferably, the mixture of methyl acetate and diethyl ether is approximately 25:75 (v/v). Also in this alternative, the aqueous phase enriched in procyanidin trimers, tetramers and pentamers is extracted with ethyl acetate and the phases are separated. The aqueous phase is enriched in procyanidin pentamers and the ethyl acetate phase is enriched in procyanidin trimers and tetramers.

In a further embodiment, the aqueous phase enriched in procyanidin dimers and higher oligomers is extracted with methyl acetate and the phases are separated. The aqueous phase is enriched in procyanidin nonamers and higher oligomers and the methyl acetate phase is enriched in procyanidin dimers, trimers, tetramers, pentamers, hexamers, heptamers and octamers. In this embodiment, the solvent is removed from the methyl acetate phase, a product obtained thereby is dissolved in water, and the dissolved product is extracted with an organic solvent which is either diethyl ether or a mixture of methyl acetate and diethyl ether effective to selectively extract catechin, epicatechin and procyanidin dimers. The phases are separated. The aqueous phase is enriched in procyanidin trimers, tetramers, pentamers, hexamers, heptamers and octamers and the organic phase is enriched in procyanidin dimers. Preferably, the mixture of methyl acetate and diethyl ether is approximately 25:75 (v/v). Further in this embodiment, the aqueous phase enriched in procyanidin trimers, tetramers, pentamers, hexamers, heptamers, octamers and minor amounts of nonamers is extracted with ethyl acetate and the phases are separated. The aqueous phase is enriched in procyanidin pentamers, hexamers, heptamers, octamers and minor amounts of procyanidin nonamers and the ethyl acetate phase is enriched in procyanidin trimers and tetramers. Still further in this embodiment, the aqueous phase enriched in procyanidin pentamers, hexamers, heptamers, octamers and minor amounts of procyanidin nonamers is extracted with an organic solvent which is a mixture of methyl acetate and diethyl ether effective to selectively extract catechin, epicatechin and procyanidin dimers, trimers, tetramers and pentamers, and the phases are separated. The aqueous phase is enriched in procyanidin hexamers, heptamers, and octamers and the organic phase is enriched in procyanidin pentamers. Preferably, the mixture of methyl acetate and diethyl ether is approximately 75:25 (v/v). Alternatively in this embodiment, the solvent is removed from the methyl acetate phase enriched in procyanidin dimers, trimers, tetramers, pentamers, hexamers, heptamers and octamers, the resulting product is dissolved in water, the dissolved product is extracted with an organic solvent which is a mixture of methyl acetate and diethyl ether effective to selectively extract catechin, epicatechin and procyanidin dimers, trimers tetramers and pentamers. The phases are separated. The aqueous phase is enriched in procyanidin hexamers, heptamers and octamers and the organic phase is enriched in procyanidin dimers, trimers, tetramers and pentamers. Preferably, the mixture of methyl acetate and diethyl ether is approximately 75:25 (v/v). Also in this alternative, the solvent is removed from the organic phase enriched in procyanidin dimers, trimers, tetramers and pentamers, the resulting product is dissolved in water, and the dissolved product is extracted with an organic solvent which is either diethyl ether or a mixture of methyl acetate and diethyl ether effective to selectively extract catechin, epicatechin and procyanidin dimers. The phases are separated. The aqueous phase is enriched in procyanidin trimers, tetramers and pentamers and the organic phase is enriched in procyanidin dimers. Preferably, the mixture of methyl acetate and diethyl ether is approximately 25:75 (v/v). Also in this alternative, the aqueous phase enriched in procyanidin trimers, tetramers and pentamers is extracted with ethyl acetate and the phases are separated. The aqueous phase is enriched in procyanidin pentamers and the ethyl acetate phase is enriched in procyanidin trimers and tetramers.

These and other objects and embodiments are disclosed or will be obvious from the following Detailed Description.

DETAILED DESCRIPTION OF THE INVENTION

The present invention discloses processes for selectively extracting individual or small groups of cocoa procyanidin monomers and/or oligomers from an aqueous mixture of cocoa polyphenols. In particular, the invention is directed to selective extraction of procyanidin monomers and/or oligomers via a selected sequence of acetate- and/or diethyl ether-based solvents, wherein the first extraction solvent is n-butyl acetate.

It has been shown that dissolving a cocoa polyphenol extract in water and extracting the aqueous solution with ethyl acetate will selectively extract the lower mass procyanidin oligomers (catechin, epicatechin, procyanidin dimers, trimers and tetramers). Based on these results, additional solvents and sequences of solvents that were immiscible in water and yet polar, "green," food grade, and reasonably priced, have been examined. Specifically, selective extraction of cocoa procyanidin monomers and/or oligomers with n-butyl acetate and methyl acetate has been examined, both alone and in sequence with ethyl acetate. All three acetate-based solvents can be purchased in food grade quality. This presents an advantage when the extracted oligomeric fractions are to be used in a food or pharmaceutical product.

Figure 1:
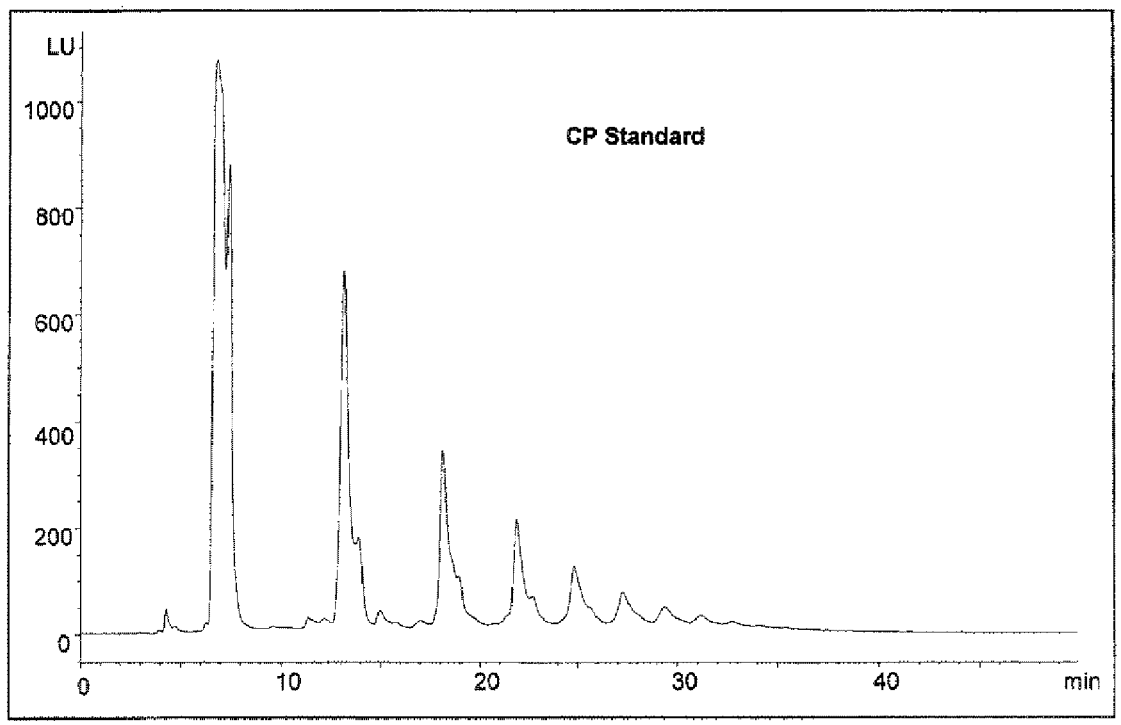
FIG. 1: HPLC chromatogram of cocoa polyphenol standard.

FIG. 1 depicts the high performance liquid chromatography (HPLC) trace of the cocoa polyphenol standard showing the individual monomers and oligomers.

Figure 2:
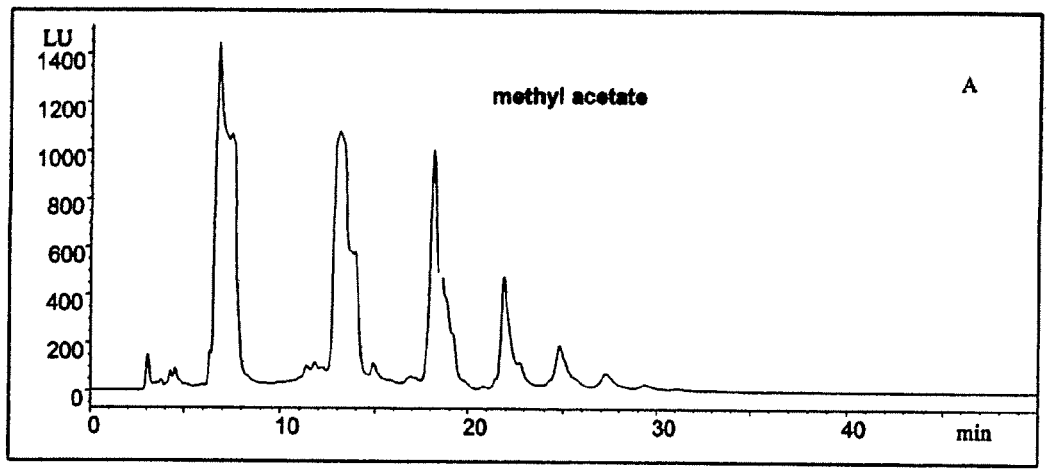
FIG. 2: HPLC/FLD chromatograms of methyl acetate organic extract fraction from aqueous cocoa polyphenol extract.
Figure 2:
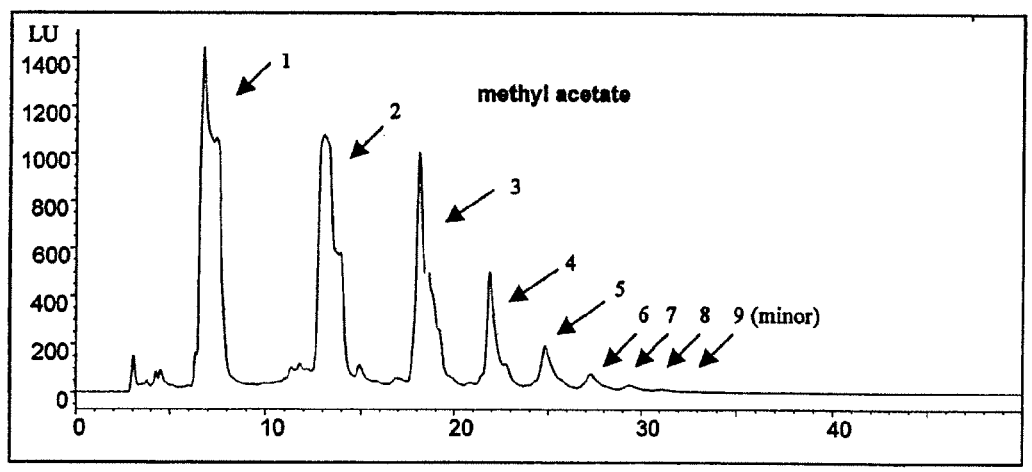

FIG. 2 shows the selective extraction profile for methyl acetate. It has been found that initial extraction of an aqueous cocoa polyphenol extract with methyl acetate will selectively extract catechin, epicatechin, and procyanidin dimers, trimers, tetramers, pentamers, hexamers, heptamers, octamers and minor amounts of procyanidin nonamers. It has also been found (not depicted) that further extraction with methyl acetate, after the lower order oligomers have been removed, will selectively extract procyanidin nonamers and higher oligomers.

Figure 3:
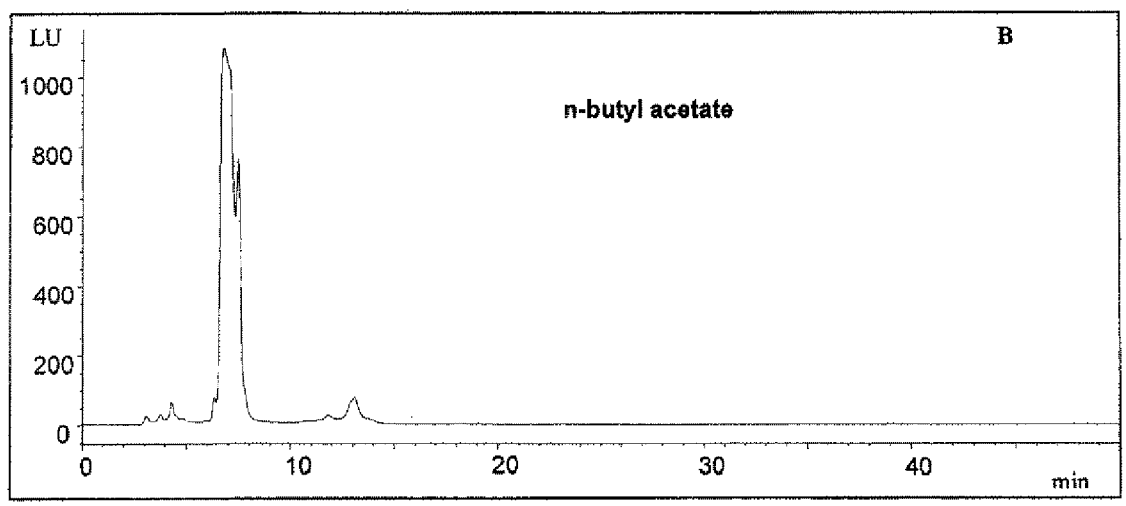
FIG. 3: HPLC/FLD chromatogram of n-butyl acetate organic extract fraction from aqueous cocoa polyphenol extract.

FIG. 3 shows the selective extraction profile for n-butyl acetate, which previously was not known. It has been found that initial extraction of an aqueous cocoa polyphenol extract with n-butyl acetate will selectively extract catechin, epicatechin and minor amounts of procyanidin dimers.

Figure 4:
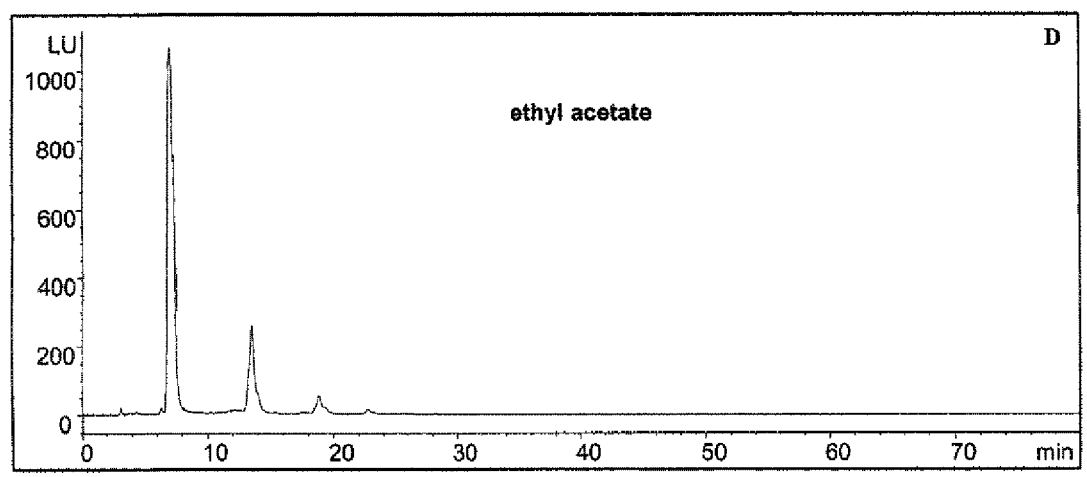
FIG. 4: HPLC/FLD chromatogram of ethyl acetate organic extract fraction from aqueous cocoa polyphenol extract.

FIG. 4 shows the selective extraction profile for ethyl acetate. As previously shown, initial extraction of an aqueous cocoa polyphenol extract with ethyl acetate will selectively extract catechin, epicatechin and procyanidin dimers, trimers and tetramers.

In addition to the three acetate-based solvents, solvents that are a mixture of methyl acetate and diethyl ether may be used to selectively extract various fractions of procyanidin oligomers from the aqueous cocoa polyphenol extract. Such diethyl ether-based solvents may have methyl acetate:diethyl ether ratios ranging from 0-100:100-0 (v/v).

Figure 5:
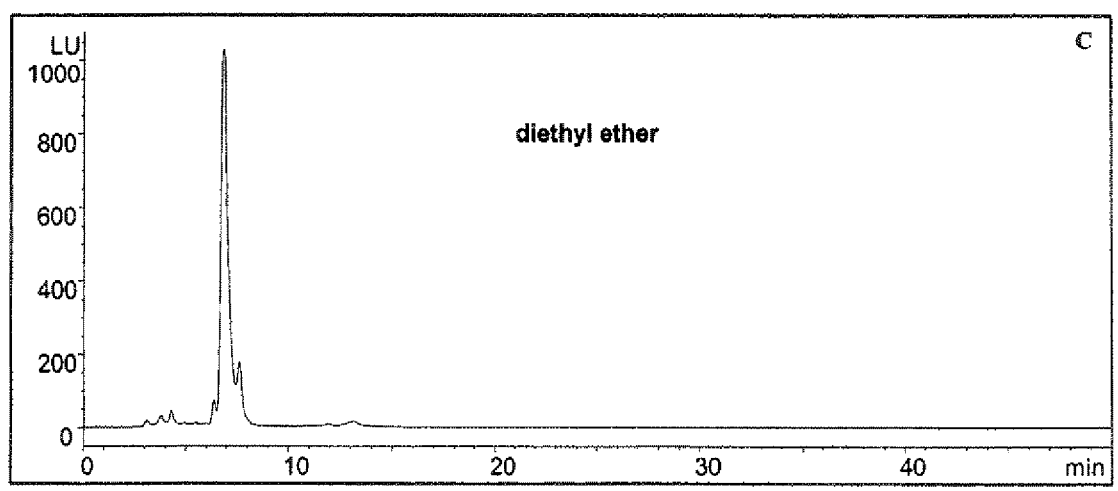
FIG. 5: HPLC/FLD chromatogram of diethyl ether organic extract fraction from aqueous cocoa polyphenol extract.
Figure 6:
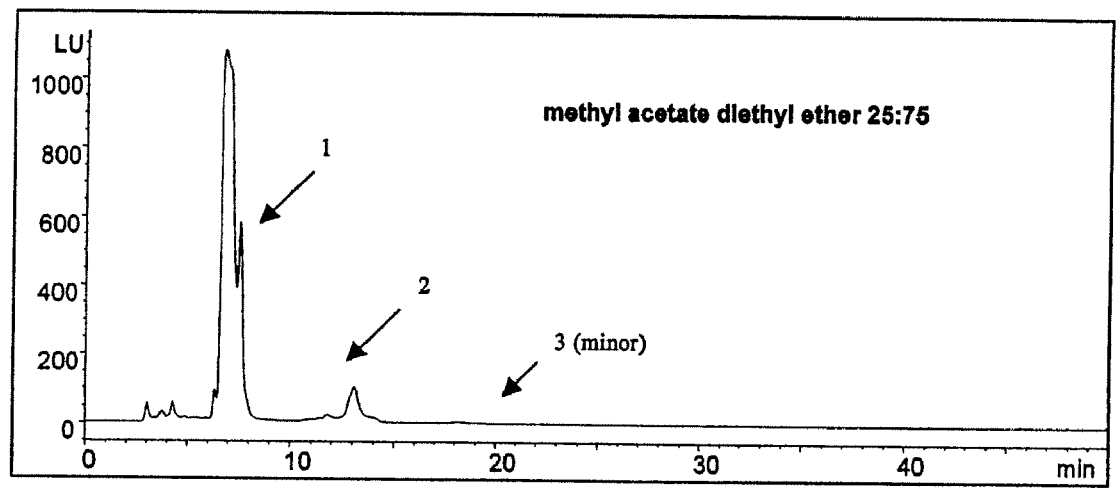
FIG. 6: HPLC/FLD chromatogram of organic extract fraction from aqueous cocoa polyphenol extract; solvent is a mixture of methyl acetate and diethyl ether (25:75 v/v).
Figure 7:
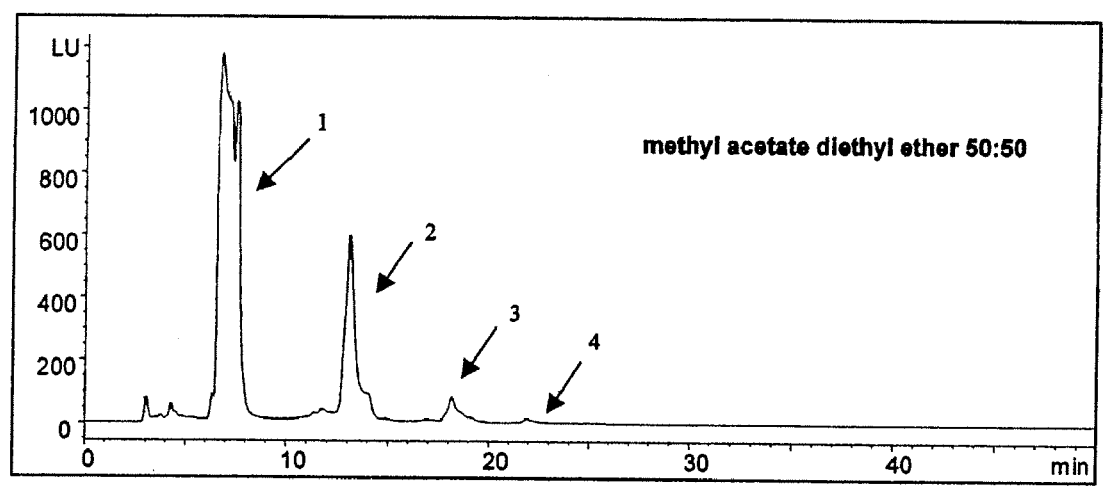
FIG. 7: HPLC/FLD chromatogram of organic extract fraction from aqueous cocoa polyphenol extract; solvent is a mixture of methyl acetate and diethyl ether (50:50 v/v).
Figure 8:
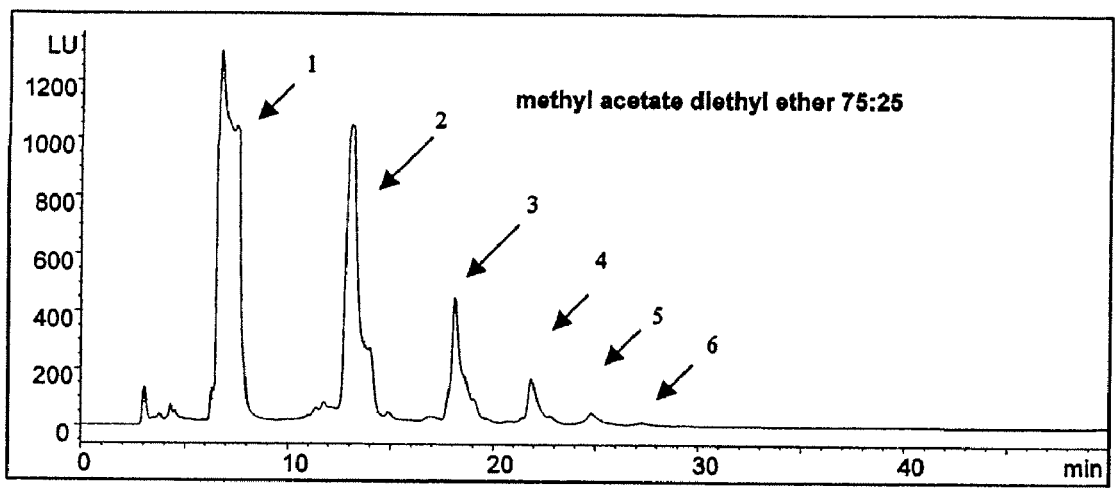
FIG. 8: HPLC/FLD chromatogram of organic extract fraction from aqueous cocoa polyphenol extract; solvent is a mixture of methyl acetate and diethyl ether (75:25 v/v).
Figure 9:
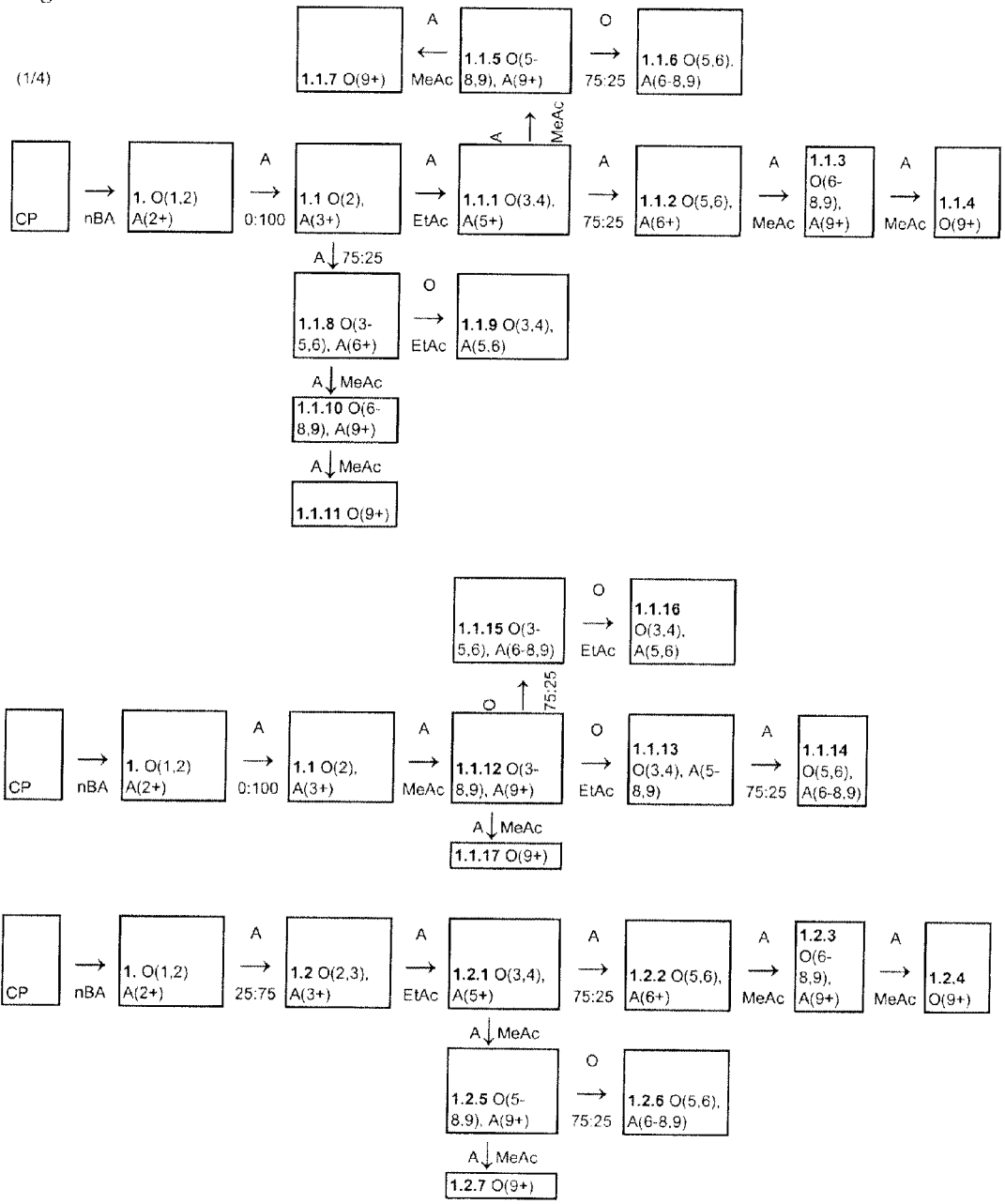
FIG. 9: Flow diagram of selective extraction pathways for selective extraction of an aqueous cocoa polyphenol extract, where the first solvent is n-butyl acetate.
Figure 9:
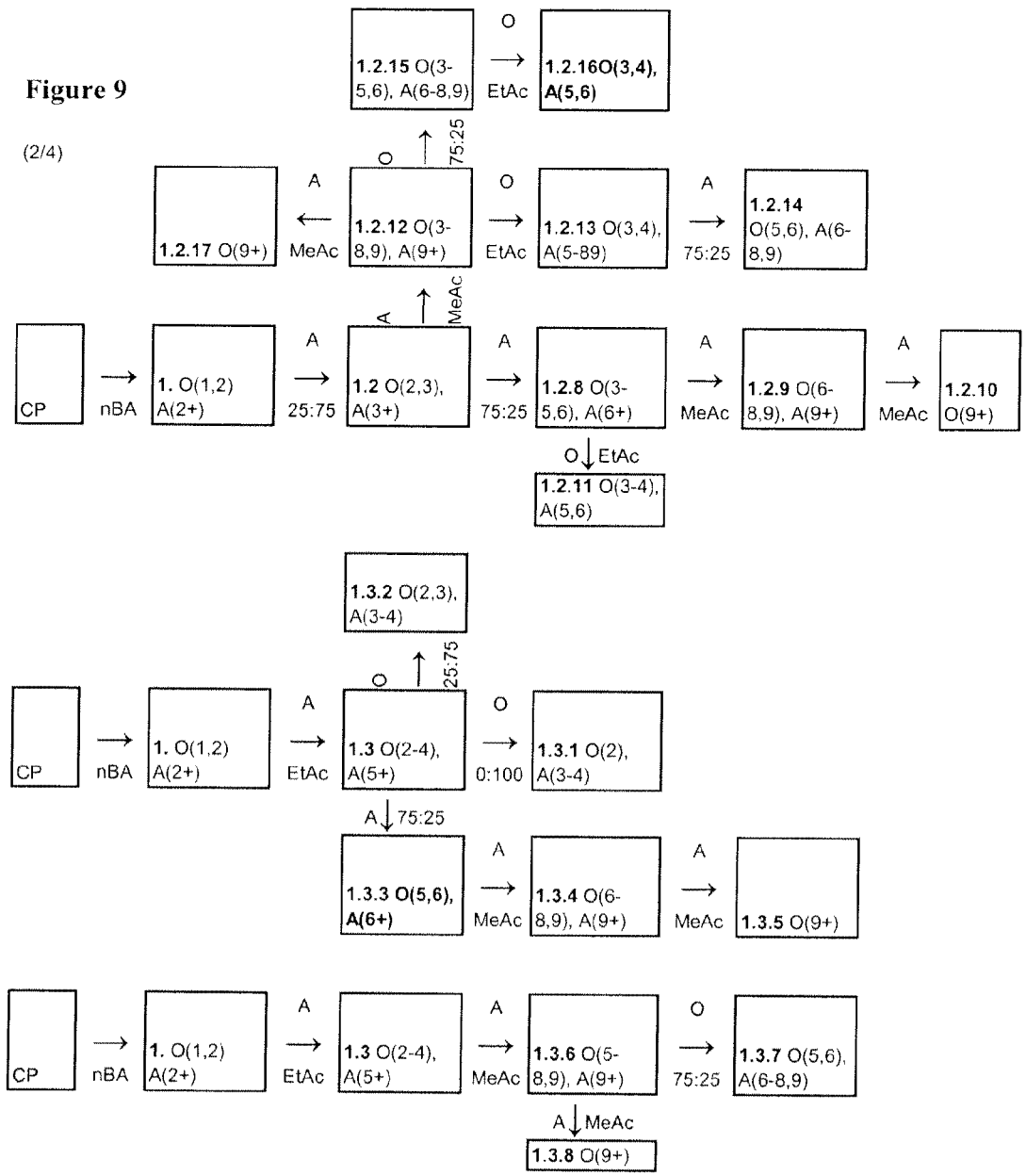
Figure 9:
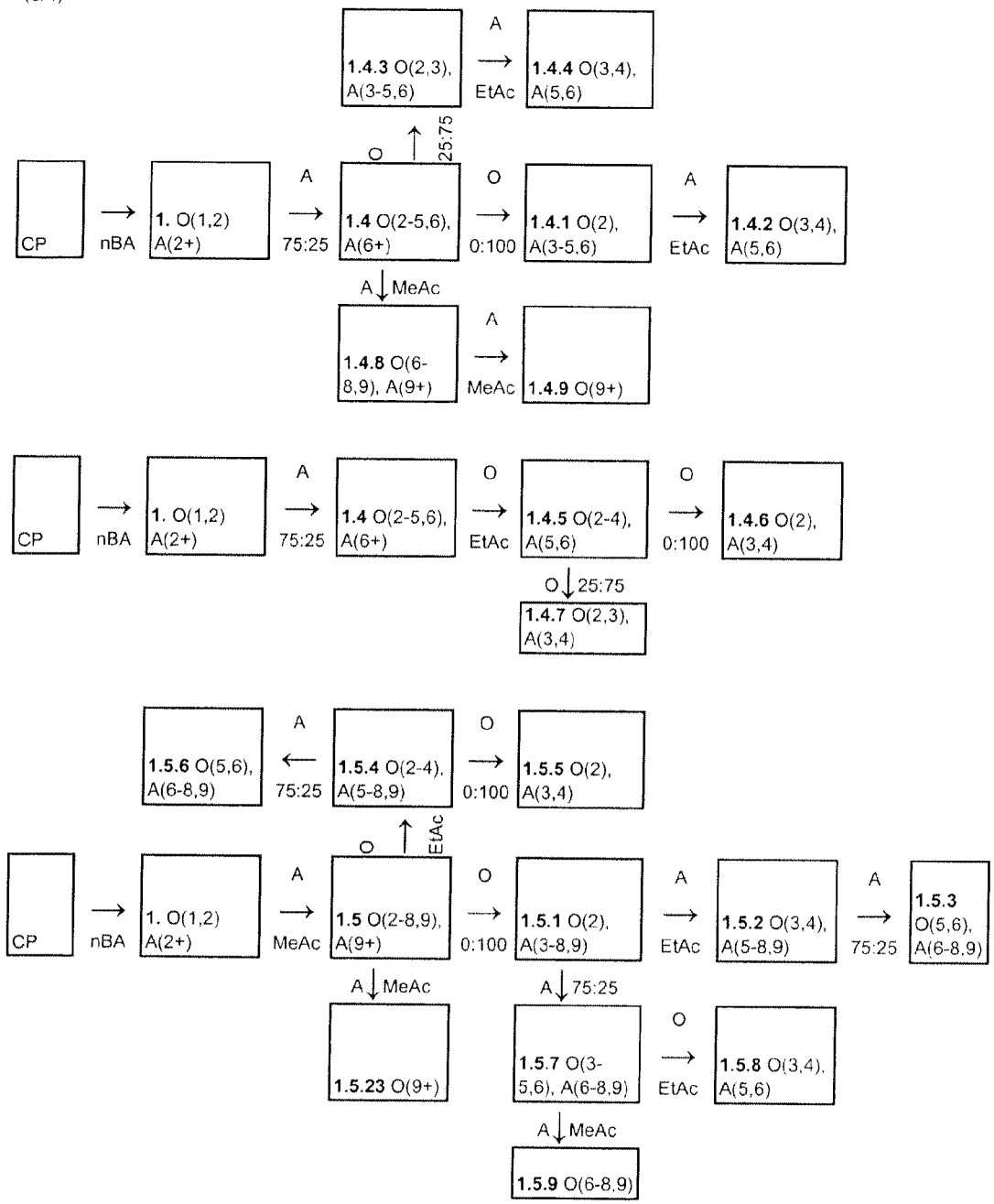
Figure 9:
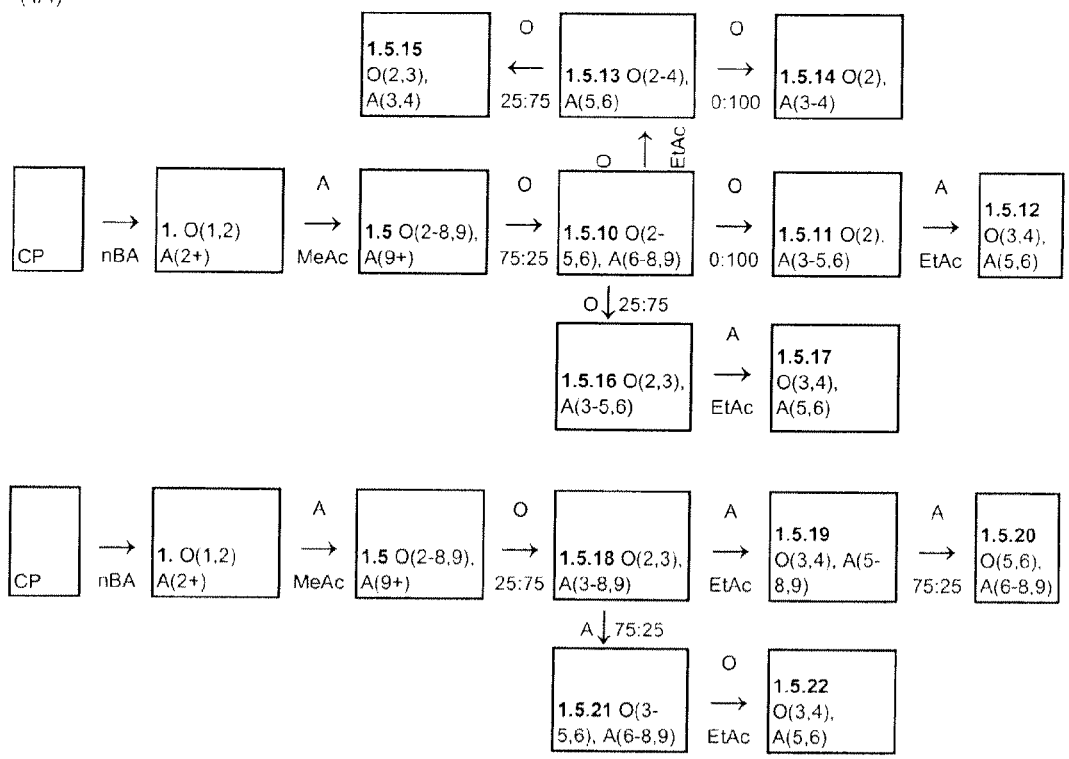

As shown in FIG. 5, where the solvent has a methyl acetate:diethyl ether ratio of 0:100 (v/v), that is, where the solvent is diethyl ether alone, the solvent selectively extracts catechin, epicatechin and procyanidin dimers from the aqueous cocoa polyphenol extract. As shown in FIG. 6, where the solvent has a methyl acetate:diethyl ether ratio of 25:75 (v/v), the solvent selectively extracts catechin, epicatechin and procyanidin dimers, along with minor amounts of procyanidin trimers. As shown in FIG. 7, where the mixed solvent has a methyl acetate:diethyl ether ratio of 50:50 (v/v), the solvent selectively extracts catechin, epicatechin and procyanidin dimers, trimers and tetramers. As shown in FIG. 8, where the mixed solvent has a methyl acetate:diethyl ether ratio of 75:25 (v/v), the solvent selectively extracts catechin, epicatechin and procyanidin dimers, trimers, tetramers, pentamers and minor amounts of procyanidin hexamers.

The table below summarizes the selection extraction profiles of the acetate- and diethyl ether-based organic solvents discussed herein.

| Solvent | Extraction profile |
| --- | --- |
| n-butyl acetate | 1, 2(minor) |
| Diethyl ether | 1-2 |
| 25:75 methyl acetate:diethyl ether | 1-2, 3(minor) |
| Ethyl acetate | 1-4 |
| 50:50 methyl acetate:diethyl ether | 1-4 |
| 75:25 methyl acetate:diethyl ether | 1-5, 6(minor) |
| Methyl acetate | 1-8, 9(minor); 9+ |

It is expected that other diethyl ether-based solvents, with other ratios of methyl acetate to diethyl ether, will selectively extract other groups of procyanidin oligomers.

There are two main factors in determining the solvents used in a particular selective extraction sequence. The first factor is the extraction profiles for the individual solvents employed. As noted, the acetate solvents (n-butyl acetate, ethyl acetate, and methyl acetate) are limited to selectively extracting, respectively: catechin, epicatechin and minor amounts of procyanidin dimers; catechin, epicatechin and procyanidin dimers, trimers and tetramers; and catechin, epicatechin and procyanidin dimers, trimers, tetramers, pentamers, hexamers, heptamers, octamers and minor amounts of procyanidin nonamers.

By contrast, the diethyl ether-based solvent group have a greater selectivity for procyanidin oligomers depending upon the proportion of diethyl ether in the solvent. For example, diethyl ether alone selectively extracts catechin, epicatechin and procyanidin dimers. A mixture of methyl acetate and diethyl ether (25:75 v/v) selectively extracts catechin, epicatechin and procyanidin dimers and minor amounts of procyanidin trimers. And a mixture of methyl acetate and diethyl ether (75:25 v/v) selectively extracts catechin, epicatechin and procyanidin dimers, trimers, tetramers, pentamers and minor amounts of procyanidin hexamers.

The second factor in determining the solvents to be used is the relative solubility of the target procyanidin oligomeric fractions in the chosen solvent. Cocoa procyanidins tend to be more soluble in an acetate-based solvent as opposed to the combined methyl acetate:diethyl ether solvent generating a similar extraction profile. For example ethyl acetate and an equal mixture of methyl acetate and diethyl ether (50:50 v/v) both selectively extract catechin, epicatechin and procyanidin dimers, trimers and tetramers from an aqueous cocoa polyphenol extract. However, ethyl acetate requires fewer extraction washes to accumulate the target polyphenols. It is known that no solvent exhaustively extracts its target polyphenols in a single extraction wash. Multiple extraction washes (as many as four) are required for the acetate solvents. By contrast, it is known that diethyl ether and diethyl ether-based solvents require further additional extraction washes (more than ten) to approach exhaustion, and may never achieve exhaustive extraction.

Therefore, where available, substituting diethyl ether-based solvents with acetate-based solvents with corresponding extraction profiles improves extraction efficiency.

Based on the selective extraction characteristics of the acetate- and diethyl ether-based solvents, various selective extraction sequences may be employed to selectively extract the desired procyanidin monomers and/or oligomer(s).

The aqueous cocoa polyphenol extract may be prepared by any conventional method. For the selective extractions where the first solvent is n-butyl acetate or methyl acetate, the aqueous cocoa polyphenol extract is prepared as follows:

Sample Preparation: cocoa polyphenol extract from defatted cocoa solids. A cocoa polyphenol extract is prepared via a multi-step process aimed at minimizing loss of the cocoa procyanidins. Cacao seeds are harvested, washed free of pulp and dried. Under ambient conditions the dried beans are expeller-pressed to remove cocoa butter. The expeller cake is then ground and extracted with ethanol:water (70:30 v/v). Solids are removed by centrifugation. The liquid extract is evaporated under reduced pressure to remove the ethanol and finally spray dried.

Sample Preparation: cocoa polyphenol extract from defatted cacao seeds. Fresh unfermented cacao seeds (30 g) are freeze-dried (16.9 g). Freeze-dried seeds (10.2 g) are defatted with hexane, and a sub-sample of the defatted beans (6.3 g) is milled and extracted thrice with 40 mL acetone:water:acetic acid (70:29.5:0.5, v/v/v) while sonicating (10 min, 50° C.). Acetone is removed from the combined extractions by rotary evaporation under reduced pressure. The remaining liquid is freeze dried to afford a red-purple residue (1.13 g).

The dried cocoa polyphenol extract is dissolved in water, preferably 50 g of extract in 200 mL of water, to provide the aqueous cocoa polyphenol extract for selective extraction, beginning with n-butyl acetate or methyl acetate.

Selectively extracted fractions were analyzed via HPLC using an Agilent 1100 HPLC system equipped with an autosampler, quaternary HPLC pump, column heater, diode array detector, and fluorescence detector. The column used was Develosil Diol (250×4.6 mm I.D., 5μ particle size) purchased from Phenomenex (Torrance, Calif.).

The binary mobile phase consisted of (A) acetonitrile: acetic acid (98:2, v/v) and (B) methanol:water:acetic acid (95:3:2, v/v/v). Separations were effected by a linear gradient (of the mobile phase) at 35° C. with an 1.0 mL/min flow rate as follows: 0-35 minutes, 0% B; 35-40 min, 40% B isocratic; 40-45 min, 40-0% B, followed by a 5 minute re-equilibrate time. Eluent was monitored by UV at 280 nm and fluorescence detection (FLD) (excitation wavelength=276 nm, emission wavelength=316 nm). Extracts and purified fractions were characterized by MS methods and parameters adapted from Hammerstone et al., J. Agric. and Food Chem. 47 (1999) 490, which are incorporated herein by reference. Ionization reagents were added via a tee in the eluant stream of the HPLC just prior to the mass spectrometer and delivered via an HPLC pump. Conditions for analysis in the positive ion mode included introduction of 0.05M NaCl at a flow rate of 0.05 mL/min to assist ionization, a capillary voltage of 3.5 kV, a fragmentor voltage of 100 V, a nebulizing pressure of 25 psig, and a drying gas temperature of 350° C. Conditions for analysis in the negative ion mode included 1.5 M ammonium hydroxide as a buffering agent at a flow rate of 0.09 mL/min for 29 minutes, and then at 0.05 mL/min. Capillary voltage was 3 kV, fragmentor voltage was 75 V, nebulizing pressure was 25 psig and drying gas temperature was 350° C.

Use of ammonium hydroxide was omitted from the MS analysis. Samples were dissolved in acetone:water:acetic acid (70:29.5:0.5, v/v/v) or mobile phase and filtered through 0.45 μm PTFE syringe filters prior to injection. All extractions were performed at room temperature. No acids were used in the extraction solvents.

In light of the non-exhaustive nature of the extraction solvents used herein, as used in the following examples, where the solvent is n-butyl acetate, ethyl acetate or methyl acetate, "extracted" will mean up to four extraction washes were performed with the solvent. When used in conjunction with diethyl ether or any mixture of diethyl ether and methyl acetate, "extracted" will mean that at least ten extraction washes were performed with the solvent. It will be understood that all organic phases from all extraction runs are combined for use or further extraction, as desired.

Also as used herein, "enriched in" shall mean the following: where the solvent is an acetate-based or diethyl ether-based organic solvent, "enriched in" shall mean that the identified phase consists essentially of the identified monomers and/or oligomers dissolved in the named solvent, together with trace amounts of other substances. Where the solvent is water, that is, where the phase at issue is the aqueous phase from an extraction step, "enriched in" shall mean that the phase consists essentially of the identified monomers and/or oligomers dissolved in water, together with trace amounts of other substances.

It will be understood by those skilled in the art that the organic and aqueous phases resulting from each of the extractions in the following examples may be separated by conventional means and the separate phases used as is, further extracted or discarded, as preferred. Where desirable, the solvent may be removed from an organic phase by conventional means and the resulting product dissolved in water to provide an aqueous mixture. It will be further understood that where an organic solvent phase (n-butyl acetate phase, ethyl acetate phase, methyl acetate phase, diethyl ether phase or other organic phase) is being extracted in an example, prior to extraction the solvent is removed from the organic phase by evaporation or other conventional means and the resulting product dissolved in water, providing an aqueous solution of the product that may then be extracted.

The following examples may be more readily understood with reference to FIGS. 9-14. In the figures, "CP" refers to the aqueous extract of cocoa polyphenols, containing catechin, epicatechin and procyanidin dimers and higher oligomers. "O" refers to the organic phase and "A" to the aqueous phase after extraction, as well as the phase (aqueous or organic) being extracted. For the solvents, "nBA" refers to n-butyl acetate; "0:100" refers to a solvent containing only diethyl ether; "25:75" refers to a diethyl ether-based solvent where the ratio of methyl acetate to diethyl ether is 25:75 (v/v); "EtAc" refers to ethyl acetate; "75:25" refers to a diethyl ether-based solvent where the ratio of methyl acetate to diethyl ether is 75:25 (v/v); and "MeAc" refers to methyl acetate, without any diethyl ether. Numbers in parentheses refer to the degree(s) of polymerization of the oligomer(s) contained in an extracted phase.

In Examples 1 through 1.5.23, the initial extraction solvent is n-butyl acetate. The examples may be better understood with reference to the flow diagrams in FIG. 9.

Example 1

Initial extraction: n-butyl acetate: An aqueous mixture of cocoa polyphenols (catechin, epicatechin, and procyanidin dimers and higher oligomers) may be extracted with n-butyl acetate. The resulting n-butyl phase is enriched in catechin and epicatechin, along with minor amounts of procyanidin dimers, and the resulting aqueous phase is enriched in procyanidin dimers and higher oligomers. Compare FIGS. 1 and 3.

Example 1.1

Second extraction: diethyl ether: The aqueous phase enriched in procyanidin dimers and higher oligomers (Example 1) may be extracted with diethyl ether to provide an organic (diethyl ether) phase enriched in procyanidin dimers and an aqueous phase enriched in procyanidin trimers and higher oligomers.

Example 1.1.1

Third extraction: ethyl acetate: The aqueous phase enriched in procyanidin trimers and higher oligomers (Example 1.1) may be extracted in ethyl acetate. The resulting ethyl acetate phase will be enriched in procyanidin trimers and tetramers while the resulting aqueous phase is enriched in procyanidin pentamers and higher oligomers.

Example 1.1.2

Fourth Extraction: Methyl acetate:diethyl Ether (75:25 v/v): The aqueous phase enriched in procyanidin pentamers and higher oligomers (Example 1.1.1) may be extracted with an organic solvent that is a mixture of methyl acetate:diethyl ether (75:25 v/v) to provide an organic phase enriched in procyanidin pentamers and an aqueous phase enriched in procyanidin hexamers and higher oligomers.

Example 1.1.3

Fifth extraction: methyl acetate: The aqueous phase enriched in procyanidin hexamers and higher oligomers (Example 1.1.2) may be extracted with methyl acetate to provide a methyl acetate phase enriched in procyanidin hexamers, heptamers, octamers and minor amounts of procyanidin nonamers and an aqueous phase enriched in procyanidin nonamers and higher oligomers.

Example 1.1.4

Sixth extraction: methyl acetate: The aqueous phase enriched in procyanidin nonamers (Example 1.1.3) may be extracted with methyl acetate to provide an organic phase enriched in procyanidin nonamers and higher oligomers. The resulting aqueous phase will be substantially depleted in procyanidins.

Example 1.1.5

Fourth extraction: methyl acetate: In a variation on Example 1.1.2, the solvent is removed from the organic phase of Example 1.1.1 by evaporation or other conventional means, and the resulting product dissolved in water. The dissolved product may be extracted with methyl acetate to provide a methyl acetate phase enriched in procyanidin pentamers, hexamers, heptamers, octamers and minor amounts of procyanidin nonamers and an aqueous phase enriched in procyanidin nonamers and higher oligomers.

Example 1.1.6

Fifth extraction: methyl acetate:diethyl ether (75:25 v/v): The solvent is removed from the methyl acetate phase of Example 1.1.5 by evaporation or other conventional means, and the resulting product dissolved in water. The dissolved product may be extracted with an organic solvent that is a mixture of methyl acetate and diethyl ether (75:25 v/v), to provide an organic phase enriched in procyanidin pentamers, with minor amounts of procyanidin hexamers. The aqueous phase will be enriched in procyanidin hexamers, heptamers, octamers and minor amounts of procyanidin nonamers.

Example 1.1.7

Fifth extraction: methyl acetate: The aqueous phase enriched in procyanidin nonamers and higher oligomers (Example 1.1.5) may be extracted with methyl acetate to provide a methyl acetate phase enriched in procyanidin nonamers and higher oligomers. The aqueous phase will be substantially depleted in procyanidins.

Example 1.1.8

Third extraction: methyl acetate:diethyl ether (75:25 v/v): In a variation on Example 1.1.1, the aqueous phase enriched in procyanidin trimers and higher oligomers (Example 1.1) may be extracted with an organic solvent comprising a mixture of methyl acetate and diethyl ether (75:25 v/v). The resulting organic phase will be enriched in procyanidin trimers, tetramers and pentamers, with minor amounts of procyanidin hexamers. The aqueous phase will be enriched in procyanidin hexamers and higher oligomers.

Example 1.1.9

Fourth extraction: ethyl acetate: The solvent is removed from the organic phase of Example 1.1.8 by evaporation or other conventional means, and the resulting product dissolved in water. The dissolved product may be extracted with ethyl acetate, providing an ethyl acetate phase enriched in procyanidin trimers and tetramers and a resulting aqueous phase enriched in procyanidin pentamers, with minor amounts of procyanidin hexamers.

Example 1.1.10

Fourth extraction: methyl acetate: The aqueous phase enriched in procyanidin hexamers and higher oligomers (Example 1.1.8) may be extracted with methyl acetate, providing a methyl acetate organic phase enriched in procyanidin hexamers, heptamers, octamers and minor amounts of procyanidin nonamers, and an aqueous phase enriched in procyanidin nonamers and higher oligomers.

Example 1.1.11

Fifth extraction: methyl acetate: The aqueous phase enriched in procyanidin nonamers and higher oligomers (Example 1.1.10) may be extracted with methyl acetate to provide a methyl acetate phase enriched in procyanidin nonamers and higher oligomers. The aqueous phase is substantially depleted of procyanidins.

Example 1.1.12

Third extraction: methyl acetate: In another variation on Example 1.1.1, the aqueous phase enriched in procyanidin trimers and higher oligomers (Example 1.1) may be extracted with methyl acetate to provide a methyl acetate phase enriched in procyanidin trimers, tetramers, pentamers, hexamers, heptamers, octamers and minor amounts of procyanidin nonamers and an aqueous phase enriched in procyanidin nonamers and higher oligomers.

Example 1.1.13

Fourth extraction: ethyl acetate: The solvent is removed from the methyl acetate phase of Example 1.1.12 by evaporation or other conventional means, and the resulting product dissolved in water. The dissolved product may be extracted with ethyl acetate to provide an ethyl acetate phase enriched in procyanidin trimers and tetramers. The aqueous phase will be enriched in procyanidin pentamers, hexamers, heptamers, octamers and minor amounts of procyanidin nonamers.

Example 1.1.14

Fifth extraction: methyl acetate:diethyl ether (75:25 v/v): The aqueous phase enriched in procyanidin pentamers, hexamers, heptamers, octamers and minor amounts of procyanidin nonamers (Example 1.1.13) may be extracted with an organic solvent that is a mixture of methyl acetate and diethyl ether (75:25 v/v) to provide an organic phase enriched in procyanidin pentamers with minor amounts of procyanidin hexamers. The aqueous phase will be enriched in procyanidin hexamers, heptamers, octamers and minor amounts of procyanidin nonamers.

Example 1.1.15

Fourth extraction: methyl acetate:diethyl ether (75:25 v/v): In a variation on Example 1.1.13, the solvent is removed from the methyl acetate phase of Example 1.1.12 by evaporation or other conventional means, and the resulting product dissolved in water. The dissolved product may be extracted with an organic solvent that is a mixture of methyl acetate and diethyl ether (75:25 v/v) to provide an organic phase enriched in procyanidin trimers, tetramers and pentamers, with a minor amount of procyanidin hexamers. The aqueous phase will be enriched in procyanidin hexamers, heptamers, octamers and minor amounts of procyanidin nonamers.

Example 1.1.16

Fifth extraction: ethyl acetate: The solvent is removed from the organic phase of Example 1.1.15 by evaporation or other conventional means, and the resulting product dissolved in water. The dissolved product may be extracted with ethyl acetate to provide an ethyl acetate phase enriched in procyanidin trimers and tetramers and an aqueous phase enriched in procyanidin pentamers, with minor amounts of procyanidin hexamers.

Example 1.1.17

Fourth extraction: methyl acetate: The aqueous phase enriched in procyanidin nonamers and higher oligomers (Example 1.1.12) may be extracted with methyl acetate. The resulting methyl acetate phase will be enriched in procyanidin nonamers and higher oligomers. The aqueous phase is substantially depleted of procyanidins.

Example 1.2

Second extraction: methyl acetate:diethyl ether (25:75 v/v): In a variation on Example 1.1, the aqueous phase enriched in procyanidin dimers and higher oligomers (Example 1) may be extracted with an organic solvent that is a mixture of methyl acetate and diethyl ether (25:75 v/v), to provide an organic phase enriched in procyanidin dimers, with minor amounts of procyanidin trimers, and an aqueous phase enriched in procyanidin trimers and higher oligomers.

Example 1.2.1

Third extraction: ethyl acetate: The aqueous phase enriched in procyanidin trimers and higher oligomers (Example 1.2) may be extracted ethyl acetate. The resulting ethyl acetate phase will be enriched in procyanidin trimers and tetramers, while the aqueous phase will be enriched in procyanidin pentamers and higher oligomers.

Example 1.2.2

Fourth extraction: methyl acetate:diethyl ether (75:25 v/v): The aqueous phase enriched in procyanidin pentamers and higher oligomers (Example 1.2.1) may be extracted with an organic solvent comprising a mixture of methyl acetate and diethyl ether (75:25 v/v), to provide an organic phase enriched in procyanidin pentamers and minor amounts of procyanidin hexamers. The aqueous phase will be enriched in procyanidin hexamers and higher oligomers.

Example 1.2.3

Fifth extraction: methyl acetate: The aqueous phase enriched in procyanidin hexamers and higher oligomers (Example 1.2.2) may be extracted with methyl acetate to provide a methyl acetate phase enriched in procyanidin hexamers, heptamers, octamers and minor amounts of procyanidin nonamers and an aqueous phase enriched in procyanidin nonamers and higher oligomers.

Example 1.2.4

Sixth extraction: methyl acetate: The aqueous phase enriched in procyanidin nonamers and higher oligomers (Example 1.2.3) may be extracted in methyl acetate. The resulting methyl acetate phase will be enriched in procyanidin nonamers and higher oligomers, while the aqueous phase will be substantially depleted of procyanidins.

Example 1.2.5

Fourth extraction: methyl acetate: In a variation of Example 1.2.2, the aqueous phase enriched in procyanidin pentamers and higher oligomers (Example 1.2.1) may be extracted with methyl acetate to provide a methyl acetate phase enriched in procyanidin pentamers, hexamers, heptamers, octamers and minor amounts of procyanidin nonamers and an aqueous phase enriched in procyanidin nonamers and higher oligomers.

Example 1.2.6

Fifth extraction: methyl acetate:diethyl ether (75:25 v/v): The solvent is removed from the organic phase of Example 1.2.5 by evaporation or other conventional means, and the resulting product dissolved in water. The dissolved product may be extracted with an organic solvent comprising a mixture of methyl acetate and diethyl ether (75:25 v/v). The resulting organic phase will be enriched in procyanidin pentamers, with minor amounts of procyanidin hexamers. The aqueous phase will be enriched in procyanidin hexamers, heptamers, octamers and minor amounts of procyanidin nonamers.

Example 1.2.7

Fifth extraction: methyl acetate: The aqueous phase enriched in procyanidin nonamers and higher oligomers (Example 1.2.5) may be extracted with methyl acetate to provide a methyl acetate phase enriched in procyanidin nonamers and higher oligomers. The aqueous phase will be substantially depleted of procyanidins.

Example 1.2.8

Third extraction: methyl acetate:diethyl ether (75:25 v/v): In a variation on Example 1.2.1, the aqueous phase enriched in procyanidin trimers and higher oligomers (Example 1.2) may be extracted with an organic solvent comprising a mixture of methyl acetate and diethyl ether (75:25 v/v). The resulting organic phase will be enriched in procyanidin trimers, tetramers and pentamers, with minor amounts of procyanidin hexamers. The aqueous phase will be enriched in procyanidin hexamers and higher oligomers.

Example 1.2.9

Fourth extraction: methyl acetate: The aqueous phase procyanidin hexamers and higher oligomers (Example 1.2.8) may be extracted with methyl acetate. The resulting methyl acetate phase will be enriched in procyanidin hexamers, heptamers, octamers and minor amounts of procyanidin nonamers, and the aqueous phase will be enriched in procyanidin nonamers and higher oligomers.

Example 1.2.10

Fifth extraction: methyl acetate: The aqueous phase enriched in procyanidin nonamers and higher oligomers (Example 1.2.9) may be extracted with methyl acetate. The resulting methyl acetate phase will be enriched in procyanidin nonamers and higher oligomers, while the aqueous phase will be substantially depleted of procyanidins.

Example 1.2.11

Fourth extraction: ethyl acetate: The solvent is removed from the organic phase of Example 1.2.8 by evaporation or other conventional means, and the resulting product dissolved in water. The dissolved product may be extracted with ethyl acetate. The resulting ethyl acetate phase will be enriched in procyanidin trimers and tetramers, while the aqueous phase will be enriched in procyanidin pentamers, with minor amounts of procyanidin hexamers.

Example 1.2.12

Third extraction: methyl acetate: In another variation on Example 1.2.1, the aqueous phase enriched in procyanidin trimers and higher oligomers (Example 1.2) may be extracted with methyl acetate. The resulting methyl acetate phase will be enriched in procyanidin trimers, tetramers, pentamers, hexamers, heptamers, octamers and minor amounts of procyanidin nonamers, while the aqueous phase will be enriched in procyanidin nonamers and higher oligomers.

Example 1.2.13

Fourth extraction: ethyl acetate: The solvent is removed from the methyl acetate phase of Example 1.2.12 by evaporation or other conventional means, and the resulting product dissolved in water. The dissolved product may be extracted with ethyl acetate. The resulting ethyl acetate phase will be enriched in procyanidin trimers and tetramers, while the aqueous phase will be enriched in procyanidin pentamers, hexamers, heptamers, octamers and minor amounts of procyanidin nonamers.

Example 1.2.14

Fifth extraction: methyl acetate:diethyl ether (75:25 v/v): The aqueous phase enriched in procyanidin pentamers, hexamers, heptamers, octamers and minor amounts of procyanidin nonamers (Example 1.2.13) may be extracted with an organic solvent comprising a mixture of methyl acetate and diethyl ether (75:25 v/v). The resulting organic phase will be enriched in procyanidin pentamers, with minor amounts of procyanidin hexamers. The aqueous phase will be enriched in procyanidin hexamers, heptamers, octamers and minor amounts of procyanidin nonamers.

Example 1.2.15

Fourth extraction: methyl acetate:diethyl ether (75:25 v/v): In a variation on Example 1.2.13, the solvent is removed from the methyl acetate phase of Example 1.2.12 by evaporation or other conventional means, and the resulting product dissolved in water. The dissolved product may be extracted with an organic solvent comprising a mixture of methyl acetate and diethyl ether (75:25 v/v). The resulting organic phase will be enriched in procyanidin trimers, tetramers and pentamers, with minor amounts of procyanidin hexamers. The aqueous phase will be enriched in procyanidin hexamers, heptamers, octamers and minor amounts of procyanidin nonamers.

Example 1.2.16

Fifth extraction: ethyl acetate: The solvent is removed from the organic phase of Example 1.2.15 by evaporation or other conventional means, and the resulting product dissolved in water. The dissolved product may be extracted with ethyl acetate. The resulting ethyl acetate phase will be enriched in procyanidin trimers and tetramers, while the aqueous phase will be enriched in procyanidin pentamers, with minor amounts of procyanidin hexamers.

Example 1.2.17

Fourth extraction: methyl acetate: The aqueous phase enriched in procyanidin nonamers and higher oligomers (Example 1.2.12) may be extracted with methyl acetate. The resulting methyl acetate phase will be enriched in procyanidin nonamers and higher oligomers. The aqueous phase will be substantially depleted of procyanidins.

Example 1.3

Second extraction: ethyl acetate: In a further variation on Example 1.1, the aqueous phase enriched in procyanidin dimers and higher oligomers (Example 1) may be extracted with ethyl acetate to provide an ethyl acetate phase enriched in procyanidin dimers, trimers and tetramers, and an aqueous phase enriched in procyanidin pentamers and higher oligomers.

Example 1.3.1

Third extraction: diethyl ether: The solvent is removed from the ethyl acetate phase of Example 1.3 by evaporation or other conventional means, and the resulting product dissolved in water. The dissolved product may be extracted with diethyl ether to provide a diethyl ether phase enriched in procyanidin dimers and an aqueous phase enriched in procyanidin trimers and tetramers.

Example 1.3.2

Third extraction: methyl acetate:diethyl ether (25:75 v/v): Alternatively to Example 1.3.1, the solvent is removed from the ethyl acetate phase of Example 1.3 by evaporation or other conventional means, and the resulting product dissolved in water. The dissolved product may be extracted with an organic solvent comprising a mixture of methyl acetate and diethyl ether (25:75 v/v), to provide an organic phase enriched in procyanidin dimers with minor amounts of procyanidin trimers, and an aqueous phase enriched in procyanidin trimers and tetramers.

Example 1.3.3

Third extraction: methyl acetate:diethyl ether (75:25 v/v): The aqueous phase enriched in procyanidin pentamers and higher oligomers (Example 1.3) may be extracted with an organic solvent comprising a mixture of methyl acetate and diethyl ether (75:25 v/v), providing an organic phase enriched in procyanidin pentamers and a minor amount of procyanidin hexamers, and a resulting aqueous phase enriched in procyanidin hexamers and higher oligomers.

Example 1.3.4

Fourth extraction: methyl acetate: The aqueous phase enriched in procyanidin hexamers and higher oligomers (Example 1.3.3) may be extracted with methyl acetate, providing a methyl acetate phase enriched in procyanidin hexamers, heptamers, octamers and minor amounts of procyanidin nonamers, and an aqueous phase enriched in procyanidin nonamers and higher oligomers.

Example 1.3.5

Fifth extraction: methyl acetate: The aqueous phase enriched in procyanidin nonamers and higher oligomers (Example 1.3.4) may be extracted with methyl acetate to provide a methyl acetate phase enriched in procyanidin nonamers and higher oligomers. The aqueous phase will be substantially depleted of procyanidins.

Example 1.3.6

Third extraction: methyl acetate: In a variation on Example 1.3.3, the aqueous phase enriched in procyanidin pentamers and higher oligomers (Example 1.3) may be extracted with methyl acetate, to provide a methyl acetate phase enriched in procyanidin pentamers, hexamers, heptamers, octamers and minor amounts of procyanidin nonamers, and an aqueous phase enriched in procyanidin nonamers and higher oligomers.

Example 1.3.7

Fourth extraction: methyl acetate:diethyl ether (75:25 v/v): The solvent is removed from the methyl acetate phase of Example 1.3.6 by evaporation or other conventional means, and the resulting product dissolved in water. The dissolved product may be extracted with an organic solvent comprising a mixture of methyl acetate and diethyl ether (75:25 v/v). The resulting organic phase will be enriched in procyanidin pentamers with minor amounts of procyanidin hexamers. The aqueous phase will be enriched in procyanidin hexamers, heptamers, octamers and minor amounts of procyanidin nonamers.

Example 1.3.8

Fourth extraction: methyl acetate: The aqueous phase enriched in procyanidin nonamers and higher oligomers (Example 1.3.6) may be extracted in methyl acetate, providing a methyl acetate phase enriched in procyanidin nonamers and higher oligomers. The aqueous phase will be substantially depleted of procyanidins.

Example 1.4

Second extraction: methyl acetate:diethyl ether (75:25 v/v): In yet a further variation on Example 1.1, the aqueous phase enriched in procyanidin dimers and higher oligomers (Example 1) may be extracted in an organic solvent comprising a mixture of methyl acetate and diethyl ether (75:25 v/v), to provide an organic phase enriched in procyanidin dimers, trimers, tetramers and pentamers and a minor amount of procyanidin hexamers, and an aqueous phase enriched in procyanidin hexamers and higher oligomers.

Example 1.4.1

Third extraction: diethyl ether: The solvent is removed from the organic phase of Example 1.4 by evaporation or other conventional means, and the resulting product dissolved in water. The dissolved product may be extracted with diethyl ether. The resulting diethyl ether phase will be enriched in procyanidin dimers and a resulting aqueous phase enriched in procyanidin trimers, tetramers and pentamers, and a minor amount of procyanidin hexamers.

Example 1.4.2

Fourth extraction: ethyl acetate: The aqueous phase enriched in procyanidin trimers, tetramers and pentamers, and a minor amount of procyanidin hexamers (Example 1.4.1) may be extracted with ethyl acetate, yielding an ethyl acetate phase enriched in procyanidin trimers and tetramers and a resulting aqueous phase enriched in procyanidin pentamers together with a minor amount of procyanidin hexamers.

Example 1.4.3

Third extraction: methyl acetate:diethyl ether (25:75 v/v): In a variation on Example 1.4.1, the solvent is removed from the organic phase of Example 1.4 by evaporation or other conventional means, and the resulting product dissolved in water. The dissolved product may be extracted with an organic solvent comprising a mixture of methyl acetate and diethyl ether (25:75 v/v). The resulting organic phase will be enriched in procyanidin dimers and minor amounts of procyanidin trimers. The aqueous phase will be enriched in procyanidin trimers, tetramers, pentamers and minor amounts of procyanidin hexamers.

Example 1.4.4

Fourth extraction: ethyl acetate: The aqueous phase procyanidin trimers, tetramers, pentamers and minor amounts of procyanidin hexamers (Example 1.4.3) may be extracted with ethyl acetate to yield an ethyl acetate phase enriched in procyanidin trimers and tetramers an aqueous phase enriched in procyanidin pentamers and minor amounts of procyanidin hexamers.

Example 1.4.5

Third extraction: ethyl acetate: In another variation on Example 1.4.1, the solvent is removed from the organic phase of Example 1.4 by evaporation or other conventional means, the resulting product dissolved in water, and the dissolved product extracted with ethyl acetate. The resulting ethyl acetate phase will be enriched in procyanidin dimers, trimers and tetramers, while the aqueous phase will be enriched in procyanidin pentamers and minor amounts of procyanidin hexamers.

Example 1.4.6

Fourth extraction: diethyl ether: The solvent is removed from the ethyl acetate phase of Example 1.4.5 by evaporation or other conventional means, the resulting product dissolved in water, and the dissolved product is extracted with diethyl ether. The resulting diethyl ether phase will be enriched in procyanidin dimers, while the aqueous phase will be enriched in procyanidin trimers and tetramers.

Example 1.4.7

Fourth extraction: methyl acetate:diethyl ether (25:75 v/v): In a variation on Example 1.4.6, the solvent is removed from the ethyl acetate phase of Example 1.4.5 by evaporation or other conventional means, the resulting product dissolved in water, and the dissolved product is extracted with an organic solvent comprising a mixture of methyl acetate and diethyl ether (25:75 v/v). The resulting organic phase will be enriched in procyanidin dimers with a minor amount of procyanidin trimers. The aqueous phase will be enriched in procyanidin trimers and tetramers.

Example 1.4.8

Third extraction: methyl acetate: The aqueous phase enriched in procyanidin hexamers and higher oligomers (Example 1.4) may be extracted with methyl acetate, yielding a methyl acetate phase enriched in procyanidin hexamers, heptamers, octamers and minor amounts of procyanidin nonamers and an aqueous phase enriched in procyanidin nonamers and higher oligomers.

Example 1.4.9

Fourth extraction: methyl acetate: The aqueous phase enriched in procyanidin nonamers and higher oligomers (Example 1.4.8) may be extracted with methyl acetate, yielding a methyl acetate phase enriched in procyanidin nonamers and higher oligomers. The aqueous phase is substantially depleted of procyanidins.

Example 1.5

Second extraction: methyl acetate: In yet another variation on Example 1.1, the aqueous phase enriched in procyanidin dimers and higher oligomers (Example 1) may be extracted with methyl acetate, to provide a methyl acetate phase enriched in procyanidin dimers, trimers, tetramers, pentamers, hexamers, heptamers, octamers and minor amounts of procyanidin nonamers, and an aqueous phase enriched in procyanidin nonamers and higher oligomers.

Example 1.5.1

Third extraction: diethyl ether: The solvent is removed from the methyl acetate phase of Example 1.5 by evaporation or other conventional means, and the resulting product dissolved in water. The dissolved product may be extracted with diethyl ether, to provide a diethyl ether phase enriched in procyanidin dimers, and an aqueous phase enriched in procyanidin trimers, tetramers, pentamers, hexamers, heptamers, octamers and minor amounts of procyanidin nonamers.

Example 1.5.2

Fourth extraction: ethyl acetate: The aqueous phase enriched in procyanidin trimers, tetramers, pentamers, hexamers, heptamers, octamers and minor amounts of procyanidin nonamers (Example 1.5.1) may be extracted with ethyl acetate, to provide an ethyl acetate phase enriched in procyanidin trimers and tetramers, and an aqueous phase enriched in procyanidin pentamers, hexamers, heptamers and minor amounts of procyanidin nonamers.

Example 1.5.3

Fifth extraction: methyl acetate:diethyl ether (75:25 v/v): The aqueous phase enriched in procyanidin pentamers, hexamers, heptamers, octamers and minor amounts of procyanidin nonamers (Example 1.5.2) may be extracted with an organic solvent comprising a mixture of methyl acetate and diethyl ether (75:25 v/v). The resulting organic phase will be enriched in procyanidin pentamers and minor amounts of procyanidin hexamers, while the aqueous phase will be enriched in procyanidin hexamers, heptamers, octamers and minor amounts of procyanidin nonamers.

Example 1.5.4

Third extraction: ethyl acetate: In a variation on Example 1.5.1, the solvent is removed from the methyl acetate phase of Example 1.5 by evaporation or other conventional means, the resulting product dissolved in water, and the dissolved product is extracted with ethyl acetate. The resulting ethyl acetate phase will be enriched in procyanidin dimers, trimers and tetramers, while the aqueous phase will be enriched in procyanidin pentamers, hexamers, heptamers, octamers and minor amounts of procyanidin nonamers.

Example 1.5.5

Fourth extraction: diethyl ether: The solvent is removed from the ethyl acetate phase of Example 1.5.4 by evaporation or other conventional means, the resulting product dissolved in water, and the dissolved product is extracted with diethyl ether. The resulting diethyl ether phase will be enriched in procyanidin dimers, while the aqueous phase will be enriched in procyanidin trimers and tetramers.

Example 1.5.6

Fourth extraction: methyl acetate:diethyl ether (75:25 v/v): The aqueous phase enriched in procyanidin pentamers, hexamers, heptamers, octamers and minor amounts of procyanidin nonamers (Example 1.5.4) may be extracted with an organic solvent comprising a mixture of methyl acetate and diethyl ether (75:25 v/v). The resulting organic phase will be enriched in procyanidin pentamers and minor amounts of procyanidin hexamers, while the aqueous phase will be enriched in procyanidin hexamers, heptamers, octamers and minor amounts of procyanidin nonamers.

Example 1.5.7

Fourth extraction: methyl acetate:diethyl ether (75:25 v/v): The aqueous phase enriched procyanidin trimers, tetramers, pentamers, hexamers, heptamers, octamers and minor amounts of procyanidin nonamers (Example 1.5.1) may be extracted with an organic solvent comprising a mixture of methyl acetate and diethyl ether (75:25 v/v). The resulting organic phase will be enriched in procyanidin trimers, tetramers and pentamers and minor amounts of procyanidin hexamers, while the aqueous phase will be enriched in procyanidin hexamers, heptamers, octamers and minor amounts of procyanidin nonamers.

Example 1.5.8

Fifth extraction: ethyl acetate: The solvent is removed from the organic phase of Example 1.5.7 by evaporation or other conventional means, the resulting product dissolved in water, and the dissolved product is extracted with ethyl acetate. The resulting ethyl acetate phase will be enriched in trimers and tetramers, while the aqueous phase will be enriched in procyanidin pentamers and minor amounts of procyanidin hexamers.

Example 1.5.9

Fifth extraction: methyl acetate: The aqueous phase enriched in procyanidin hexamers, heptamers, octamers and minor amounts of procyanidin nonamers (Example 1.5.7) may be extracted with methyl acetate. The resulting methyl acetate phase will be enriched in procyanidin hexamers, heptamers, octamers and minor amounts of procyanidin nonamers. The aqueous phase will be substantially depleted of procyanidins.

Example 1.5.10

Third extraction: methyl acetate:diethyl ether (75:25 v/v): In another variation on Example 1.5.1, the solvent is removed from the methyl acetate phase of Example 1.5 by evaporation or other conventional means, the resulting product dissolved in water, and the dissolved product is extracted with an organic solvent comprising a mixture of methyl acetate and diethyl ether (75:25 v/v). The resulting organic phase will be enriched in procyanidin dimers, trimers, tetramers and pentamers and minor amounts of procyanidin hexamers, while the aqueous phase will be enriched in procyanidin hexamers, heptamers, octamers and minor amounts of procyanidin nonamers.

Example 1.5.11

Fourth extraction: diethyl ether: The solvent is removed from the organic phase of Example 1.5.10 by evaporation or other conventional means, the resulting product dissolved in water, and the dissolved product is extracted with diethyl ether. The resulting diethyl ether phase will be enriched in procyanidin dimers while the aqueous phase will be enriched in procyanidin trimers, tetramers, pentamers and minor amounts of procyanidin hexamers.

Example 1.5.12

Fifth extraction: ethyl acetate: The aqueous phase enriched in procyanidin trimers, tetramers pentamers and minor amounts of procyanidin hexamers (Example 1.5.11) may be extracted with ethyl acetate. The resulting ethyl acetate phase will be enriched in procyanidin trimers and tetramers, while the aqueous phase will be enriched in procyanidin pentamers and minor amounts of procyanidin hexamers.

Example 1.5.13

Fourth extraction: ethyl acetate: In a variation on Example 1.5.11, the solvent is removed from the organic phase of Example 1.5.10 by evaporation or other conventional means, the resulting product dissolved in water, and the dissolved product is extracted with ethyl acetate. The resulting ethyl acetate phase will be enriched in procyanidin dimers, trimers and tetramers, while the aqueous phase will be enriched in procyanidin pentamers and minor amounts of procyanidin hexamers.

Example 1.5.14

Fifth extraction: diethyl ether: The solvent is removed from the ethyl acetate phase of Example 1.5.13 by evaporation or other conventional means, the resulting product dissolved in water, and the dissolved product is extracted with diethyl ether. The resulting diethyl ether phase will be enriched in procyanidin dimers, while the aqueous phase will be enriched in procyanidin trimers and tetramers.

Example 1.5.15

Fifth extraction: methyl acetate:diethyl ether (25:75 v/v): In a variation on Example 1.5.14, the solvent is removed from the ethyl acetate phase of Example 1.5.13 by evaporation or other conventional means, the resulting product dissolved in water, and the dissolved product is extracted with an organic solvent comprising a mixture of methyl acetate and diethyl ether (25:75 v/v). The resulting organic phase will be enriched in dimers and minor amounts of procyanidin trimers, and the aqueous phase will be enriched in procyanidin trimers and tetramers.

Example 1.5.16

Fourth extraction: methyl acetate:diethyl ether (25:75 v/v): In another variation on Example 1.5.11, the solvent is removed from the organic phase of Example 1.5.10 by evaporation or other conventional means, the resulting product dissolved in water, and the dissolved product is extracted with an organic solvent comprising a mixture of methyl acetate and diethyl ether (25:75 v/v). The resulting organic phase will be enriched in procyanidin dimers and minor amounts of procyanidin trimers. The aqueous phase will be enriched in procyanidin trimers, tetramers and pentamers and minor amounts of procyanidin hexamers.

Example 1.5.17

Fifth extraction: ethyl acetate: The aqueous phase enriched in procyanidin trimers, tetramers, pentamers and minor amounts of procyanidin hexamers (Example 1.5.16) may be extracted with ethyl acetate. The resulting ethyl acetate phase will be enriched in procyanidin trimers and tetramers, while the aqueous phase will be enriched in procyanidin pentamers and minor amounts of procyanidin hexamers.

Example 1.5.18

Third extraction: methyl acetate:diethyl ether (25:75 v/v): In yet another variation on Example 1.5.1, the solvent is removed from the methyl acetate phase of Example 1.5 by evaporation or other conventional means, the resulting product dissolved in water, and the dissolved product is extracted with an organic solvent comprising a mixture of methyl acetate and diethyl ether (25:75 v/v). The resulting organic phase will be enriched in procyanidin dimers and minor amounts of procyanidin trimers, while the aqueous phase will be enriched in procyanidin trimers, tetramers, pentamers, hexamers, heptamers, octamers and minor amounts of procyanidin nonamers.

Example 1.5.19

Fourth extraction: ethyl acetate: The aqueous phase enriched in procyanidin trimers, tetramers, pentamers, hexamers, heptamers, octamers and minor amounts of procyanidin nonamers (Example 1.5.18) may be extracted with ethyl acetate. The resulting ethyl acetate phase will be enriched in procyanidin trimers and tetramers, while the aqueous phase will be enriched in procyanidin pentamers, hexamers, heptamers, octamers and minor amounts of procyanidin nonamers.

Example 1.5.20

Fifth extraction: methyl acetate:diethyl ether (75:25 v/v): The aqueous phase enriched in procyanidin pentamers, hexamers, heptamers, octamers and minor amounts of procyanidin nonamers (Example 1.5.19) may be extracted with an organic solvent comprising a mixture of methyl acetate and diethyl ether (75:25 v/v). The resulting organic phase will be enriched in procyanidin pentamers and minor amounts of procyanidin hexamers, while the aqueous phase will be enriched in procyanidin hexamers, heptamers, octamers and minor amounts of procyanidin nonamers.

Example 1.5.21

Fourth extraction: methyl acetate:diethyl ether (75:25 v/v): In a variation on Example 1.5.19, the aqueous phase enriched in procyanidin trimers, tetramers, pentamers, hexamers, heptamers, octamers and minor amounts of procyanidin nonamers (Example 1.5.18) may be extracted with an organic solvent comprising a mixture of methyl acetate and diethyl ether (75:25 v/v). The resulting organic phase will be enriched in procyanidin trimers, tetramers, pentamers and minor amounts of procyanidin hexamers, while the aqueous phase will be enriched in procyanidin hexamers, heptamers, octamers and minor amounts of procyanidin nonamers.

Example 1.5.22

Fifth extraction: ethyl acetate: The solvent is removed from the organic phase of Example 1.5.21 by evaporation or other conventional means, the resulting product dissolved in water, and the dissolved product is extracted with ethyl acetate. The resulting ethyl acetate phase will be enriched in procyanidin trimers and tetramers, while the aqueous phase will be enriched in procyanidin pentamers and minor amounts of procyanidin hexamers.

Example 1.5.23

Third extraction: methyl acetate: The aqueous phase enriched in procyanidin nonamers and higher oligomers (Example 1.5) may be extracted with methyl acetate to provide a methyl acetate phase enriched in procyanidin nonamers and higher oligomers. The aqueous phase will be substantially depleted in procyanidins.

Figure 10:
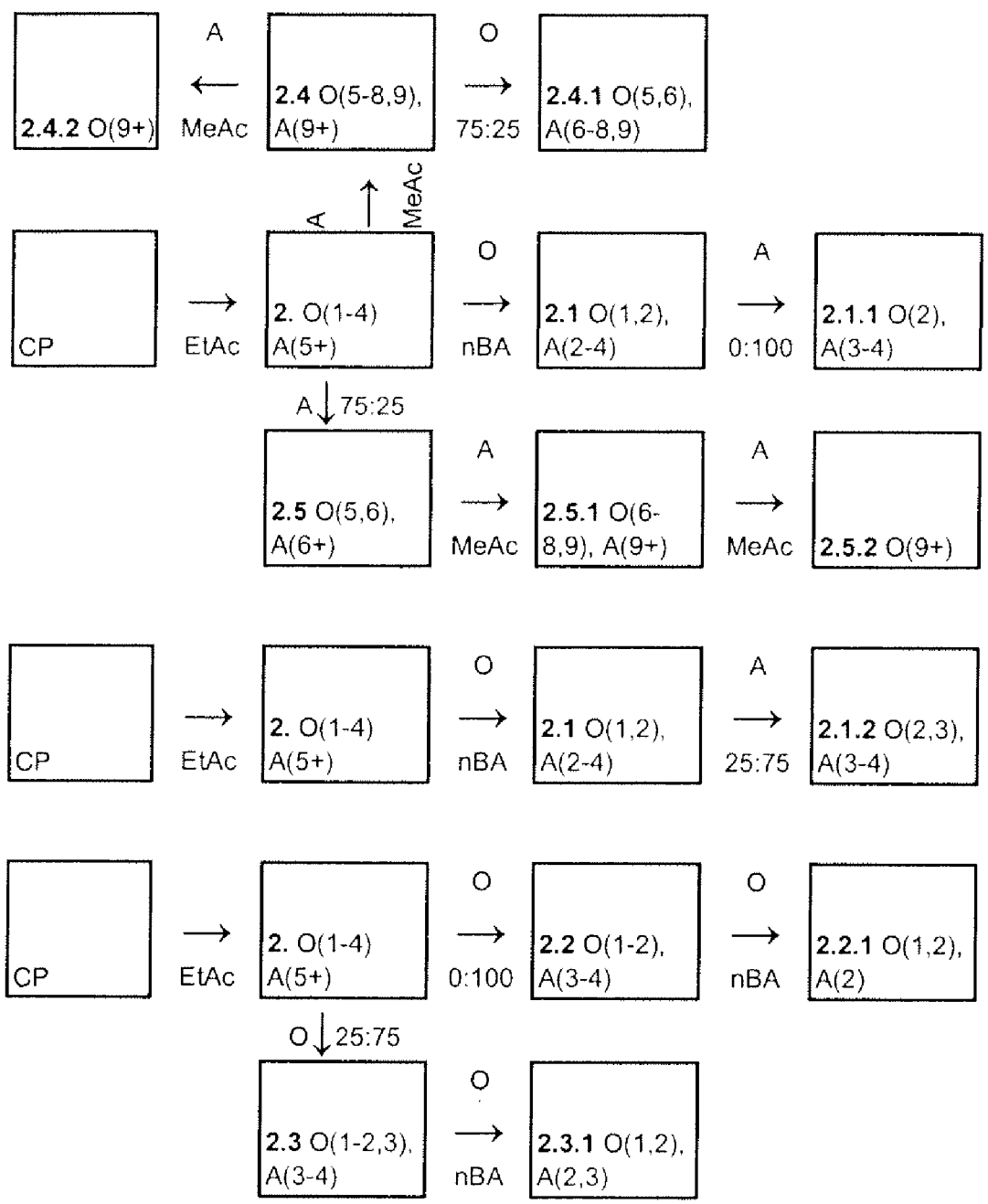
FIG. 10: Flow diagram of selective extraction pathways for selective extraction of an aqueous cocoa polyphenol extract where the first solvent is ethyl acetate.
Figure 11:
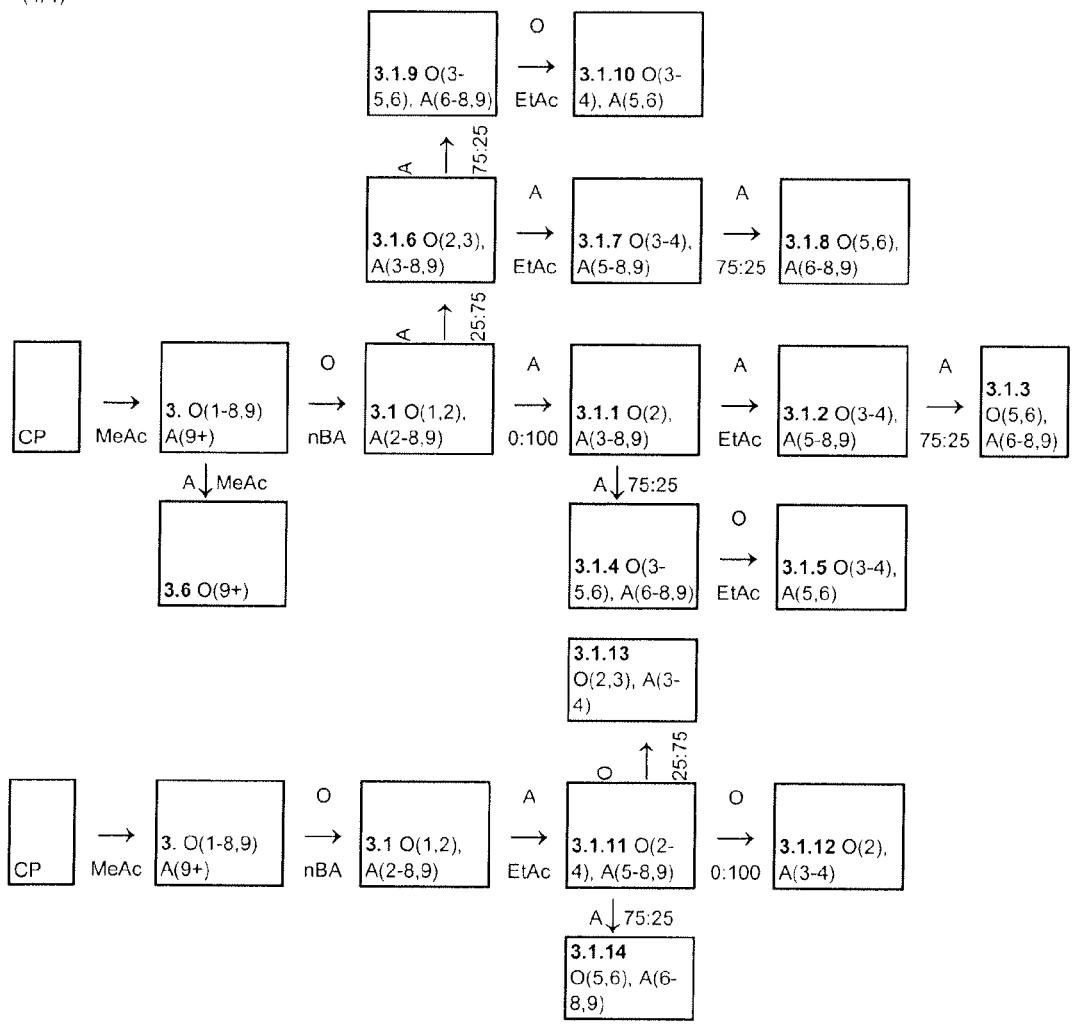
FIG. 11: Flow diagram of selective extraction pathways for selective extraction of an aqueous cocoa polyphenol extract where the first solvent is methyl acetate.
Figure 11:
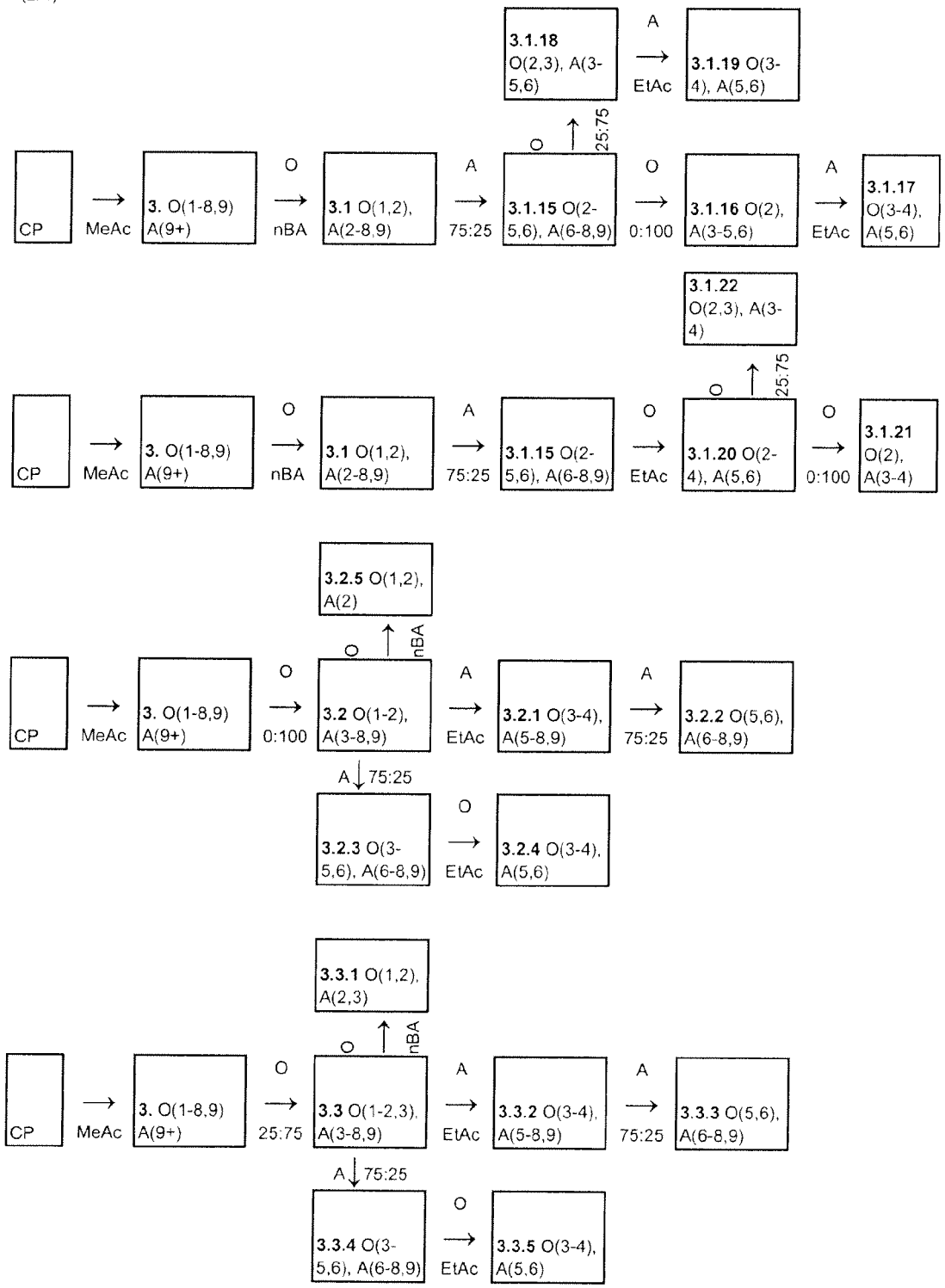
Figure 11:
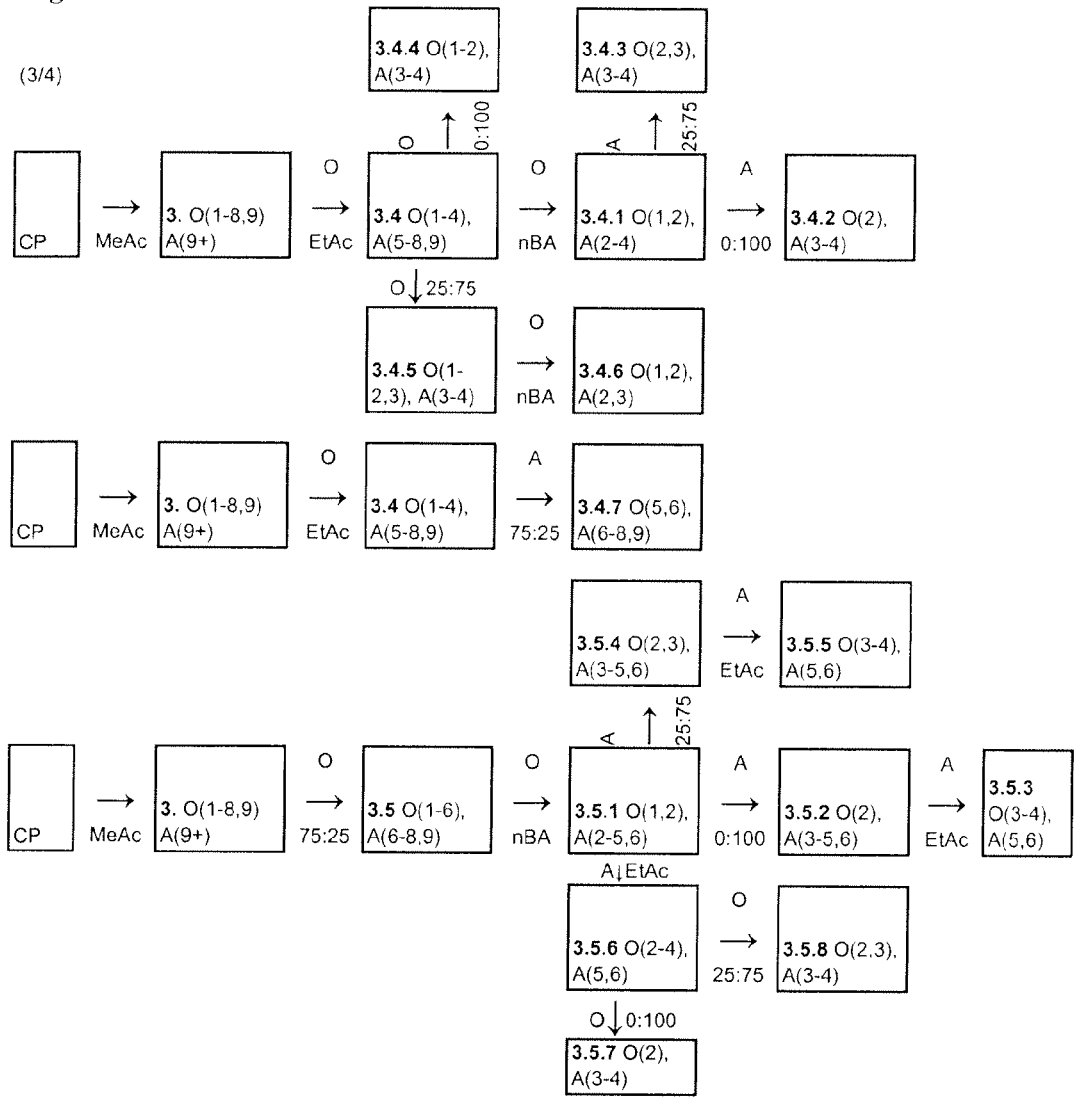
Figure 11:
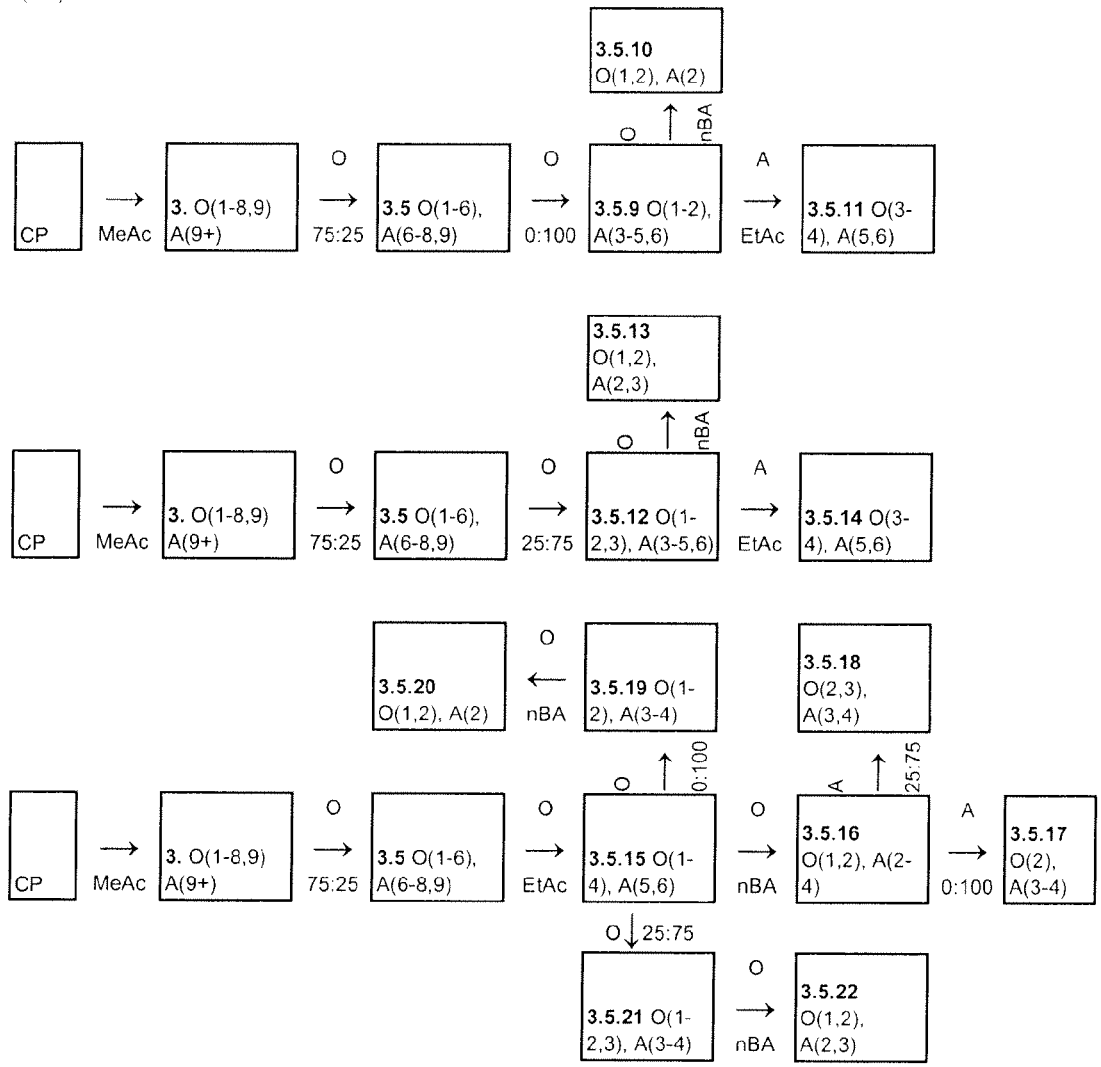
Figure 12:
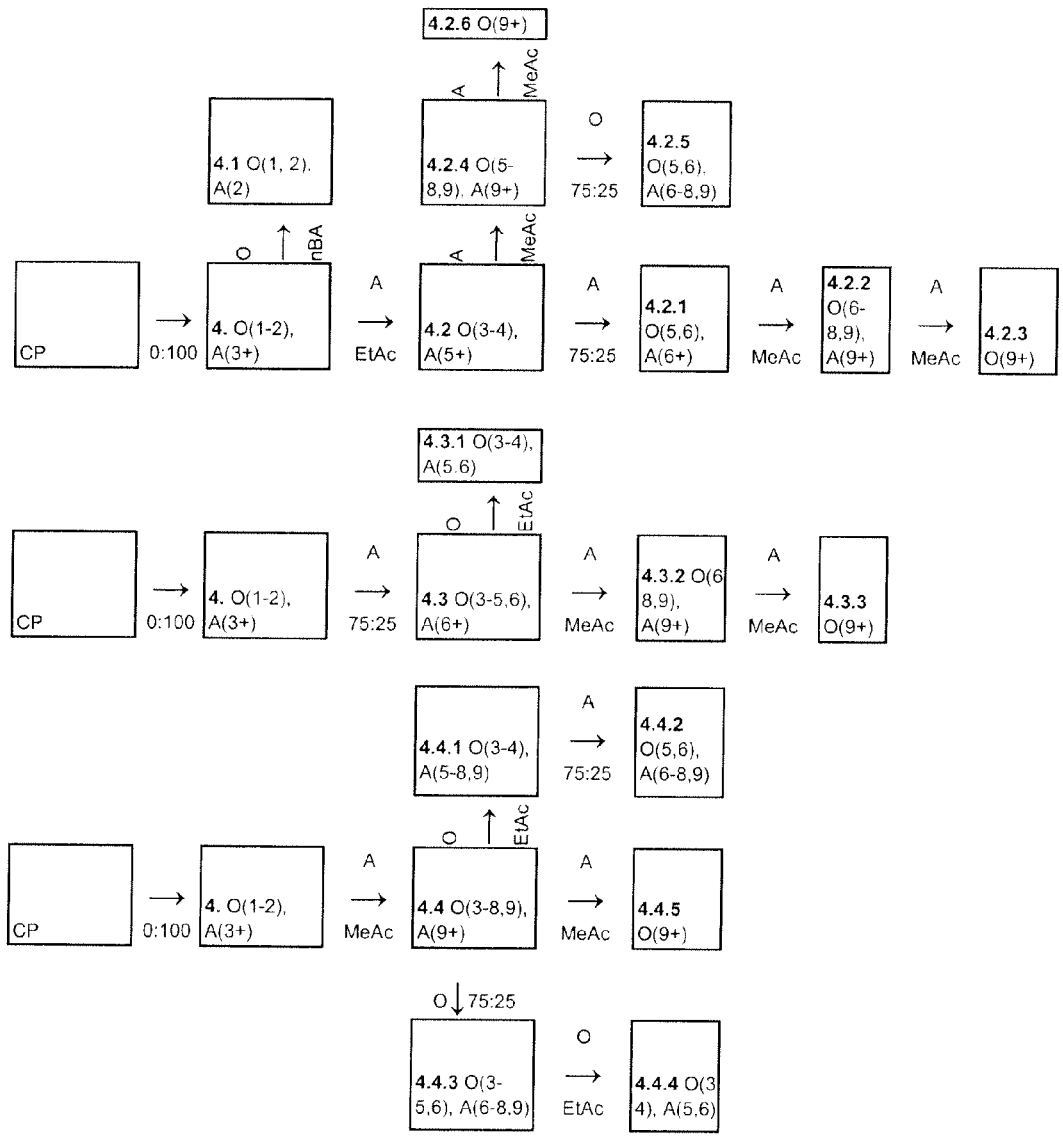
FIG. 12: Flow diagram of selective extraction pathways for selective extraction of an aqueous cocoa polyphenol extract where the first solvent is diethyl ether.
Figure 13:
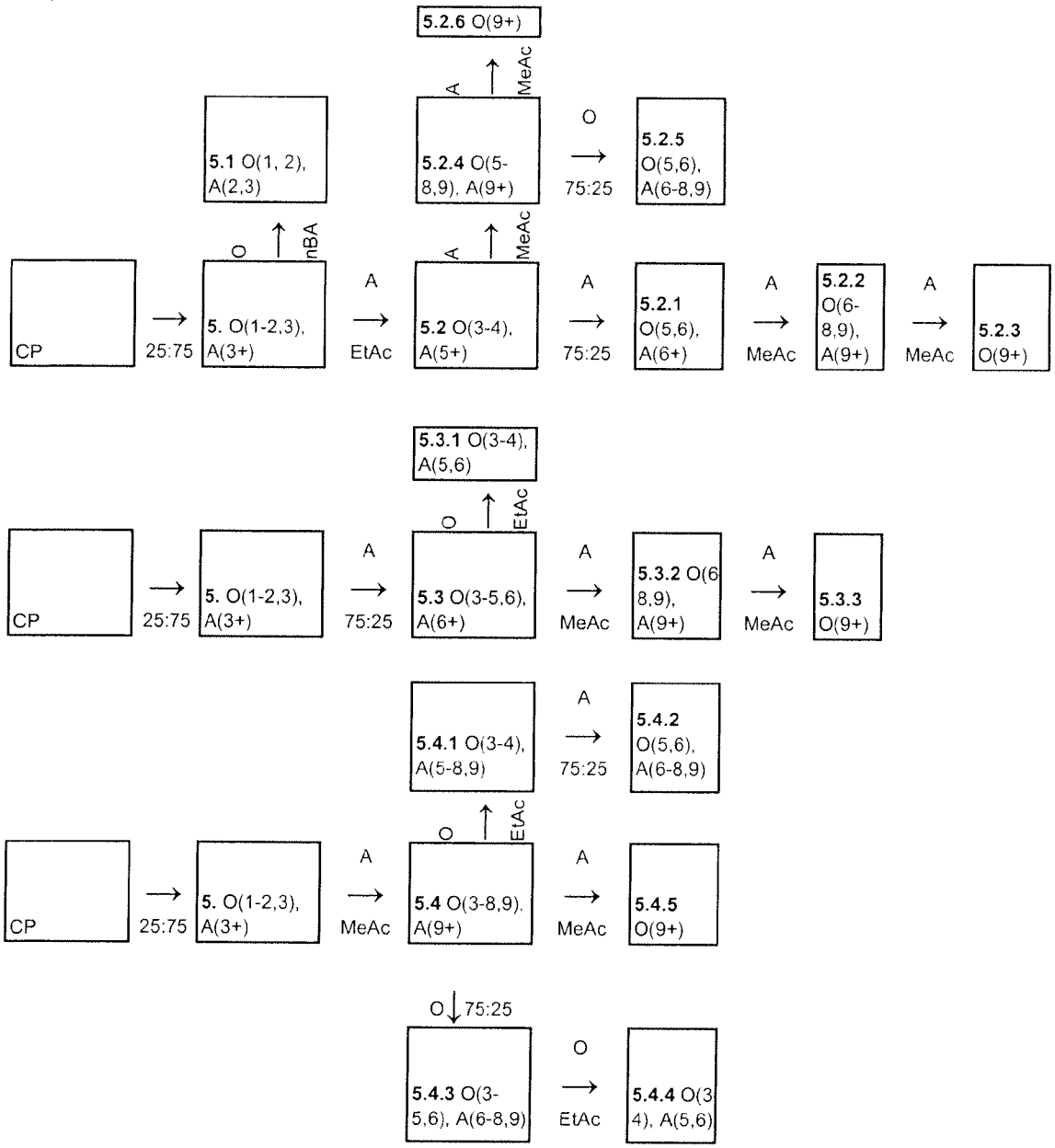
FIG. 13: Flow diagram of selective extraction pathways for selective extraction of an aqueous cocoa polyphenol extract where the first solvent is a mixture of methyl acetate and diethyl ether (25:75 v/v).
Figure 14:
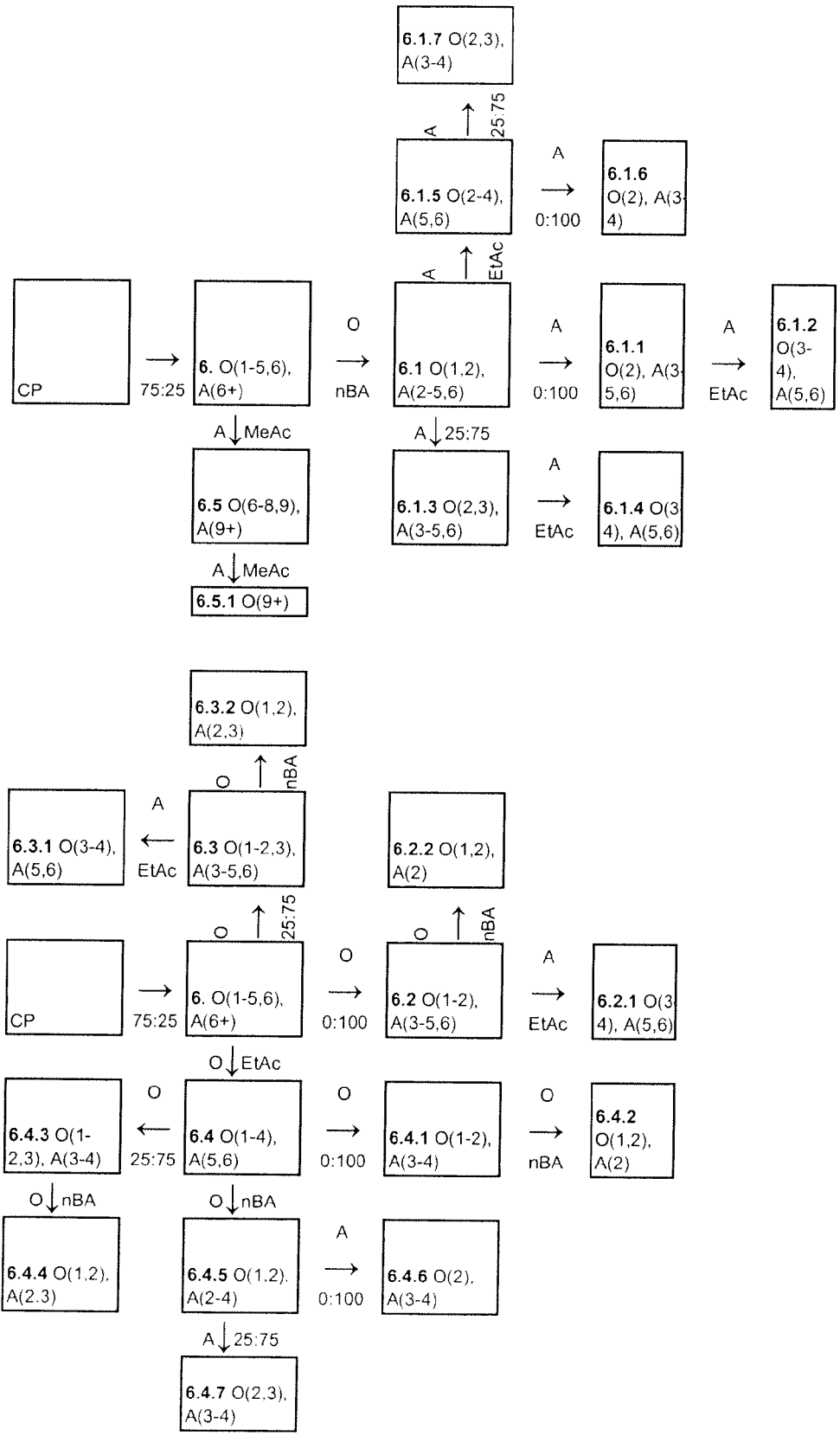
FIG. 14: Flow diagram of selective extraction pathways for selective extraction of an aqueous cocoa polyphenol extract where the first solvent is a mixture of methyl acetate and diethyl ether (75:25 v/v).

Examples of other extraction sequences, using other initial extraction solvents, are described in FIGS. 10-14. FIG. 10 depicts Examples 2 through 2.5.2, wherein the initial extraction solvent (Example 2) is ethyl acetate. FIG. 11 depicts Examples 3 through 3.6, wherein the initial extraction solvent (Example 3) is methyl acetate. FIG. 12 depicts Examples 4 through 4.4.5, wherein the initial extraction solvent is diethyl ether. FIG. 13 depicts Examples 5 through 5.4.5, wherein the initial extraction solvent is a mixture of methyl acetate and diethyl ether (25:75 v/v). FIG. 14 depicts Examples 6 through 6.5.1, wherein the initial extraction solvent is a mixture of methyl acetate and diethyl ether (75:25 v/v).

It will be understood by those skilled in the art that, while the above examples relate to selective extractions of aqueous cocoa polyphenol extracts, any substance comprising polar protic oligomers may be selectively extracted in accordance with the provided example. Suitable polar protic oligomers include proanthocyanidins, hydrolyzable tannins, oligosaccharides, oligonucleotides, peptides, acrylamides, polysorbates, polyketides, poloxamers, polyethylene glycols, polyoxyethylene alcohols and polyvinyl alcohols. Where the polar protic oligomers are proanthocyanidins, they may be proapigeninidins, proluteolinidins, protricetinidins, propelargonidins, prodelphinidins, proguibourtinidins, profisetinidins, prorobinetindins, proteracacinidins and/or promelacacinidins.

While the invention has been described with respect to certain specific embodiments, it will be appreciated that many modifications and changes may be made by those skilled in the art without departing from the invention. It is intended, therefore, by the appended to cover all such modifications and changes as may fall within the true spirit and scope of the invention.

What is claimed is:

1. A process for selectively extracting cocoa procyanidins from an aqueous mixture of cocoa polyphenols, which process comprises the steps of extracting the aqueous mixture with ethyl acetate and separating an aqueous phase enriched in procyanidin pentamers and higher oligomers and an ethyl acetate phase enriched in epicatechin, catechin, and procyanidin dimers through tetramers.

2. The process of claim 1, further comprising the steps of extracting the aqueous phase with methyl acetate and separating an aqueous phase enriched in procyanidin nonamers and higher oligomers and a methyl acetate phase enriched in procyanidin pentamers through nonamers.

3. The process of claim 2, further comprising the steps of extracting the aqueous phase with methyl acetate and separating a methyl acetate phase enriched in procyanidin nonamers and higher oligomers.

4. The process of claim 1, further comprising the steps of removing the solvent from the ethyl acetate phase, dissolving the resulting product in water, extracting the aqueous solution with n-butyl acetate, and separating an aqueous phase enriched in procyanidin dimers through tetramers and an n-butyl acetate phase enriched in epicatechin, catechin, and procyanidin dimers.

5. A process for selectively extracting cocoa procyanidins from an aqueous mixture of cocoa polyphenols, which process comprises the steps of extracting the aqueous mixture with methyl acetate and separating an aqueous phase enriched in procyanidin nonamers and higher oligomers and a methyl acetate phase enriched in epicatechin, catechin, and procyanidin dimers through nonamers.

6. The process of claim 5, further comprising the steps of extracting the aqueous phase with methyl acetate and separating a methyl acetate phase enriched in procyanidin nonamers and higher oligomers.

7. The process of claim 5, further comprising the steps of removing the solvent from the methyl acetate phase, dissolving the resulting product in water, extracting the aqueous solution with n-butyl acetate, and separating an aqueous phase enriched in procyanidin dimers through nonamers and an n-butyl acetate phase enriched in epicatechin, catechin, and procyanidin dimers.

8. The process of claim 7, further comprising the steps of extracting the aqueous phase with ethyl acetate and separating an aqueous phase enriched in procyanidin pentamers through nonamers and an ethyl acetate phase enriched in procyanidin dimers through tetramers.

9. The process of claim 5, further comprising the steps of removing the solvent from the methyl acetate phase, dissolving the resulting product in water, extracting the aqueous solution with ethyl acetate, and separating an aqueous phase enriched in procyanidin pentamers through nonamers and an ethyl acetate phase enriched in epicatechin, catechin, and procyanidin dimers through tetramers.

10. The process of claim 9, further comprising the steps of removing the solvent from the ethyl acetate phase, dissolving the resulting product in water, extracting the aqueous solution with n-butyl acetate, and separating an aqueous phase enriched in procyanidin dimers through tetramers and an n-butyl acetate phase enriched in epicatechin, catechin, and procyanidin dimers.

* * * * *